United States Patent
Chen et al.

(10) Patent No.: US 8,354,234 B2
(45) Date of Patent: Jan. 15, 2013

(54) MASS SPECTROMETRIC ANALYSIS OF LIGAND CONJUGATED MAGNETIC NANOPARTICLES

(75) Inventors: Yu-Ju Chen, Lugang Township, Changhua County (TW); Po-Chiao Lin, Pingtung (TW); Chun-Cheng Lin, Fongyuan (TW); Shu-Hua Chen, Taipei (TW); Po-Hung Chou, Taipei County (TW); Hsin-Kai Liao, Taipei (TW)

(73) Assignee: Academia Sinica, Taipei (TW)

( * ) Notice: Subject to any disclaimer, the term of this patent is extended or adjusted under 35 U.S.C. 154(b) by 1183 days.

(21) Appl. No.: 11/487,823

(22) Filed: Jul. 17, 2006

(65) Prior Publication Data
US 2007/0054407 A1 Mar. 8, 2007

Related U.S. Application Data

(60) Provisional application No. 60/701,379, filed on Jul. 21, 2005.

(51) Int. Cl.
G01N 33/53 (2006.01)
G01N 33/543 (2006.01)
G01N 33/553 (2006.01)

(52) U.S. Cl. ......... 435/7.1; 435/7.92; 436/523; 436/525

(58) Field of Classification Search .................. 436/526, 436/518, 173, 538, 546, 164; 435/6
See application file for complete search history.

(56) References Cited

U.S. PATENT DOCUMENTS

| | | | | | |
|---|---|---|---|---|---|
| 5,527,713 | A | * | 6/1996 | Bolton et al. | 436/529 |
| 5,928,958 | A | * | 7/1999 | Pilgrimm | 436/526 |
| 6,231,982 | B1 | * | 5/2001 | Wang | 428/407 |
| 6,649,419 | B1 | * | 11/2003 | Anderson | 436/526 |
| 6,815,212 | B2 | * | 11/2004 | Ness et al. | 436/173 |
| 2002/0192676 | A1 | * | 12/2002 | Madonna et al. | 435/6 |

OTHER PUBLICATIONS

Girault et al. Anal. Chem. 1996, 68, 2122-2126.*
Holland et al. Rapid Communications in Mass Spectrometry, vol. 10, 1227-1232 (1996).*
Shine et al. Solid phase radioimmunoassays for human C-reactive protein. Clinica Chimica Acta 1981, pp. 13-23. Abstrat is provided.*
Jain, Kewal. Nanotechnology in clinical laboratory diagnostics. Clinica Chimica Acta 2005, vol. 358, pp. 37-54.*
Article from Chinatimes Evening News dated Jul. 20, 2005, and English Translation.
Lin, et al., "Ethylene Glycol-Protected Magnetic Nanoparticles for a Multiplexed Immunoassay in Human Plasma", Small Journal, vol. 2, No. 4, pp. 485-489 (2006).

* cited by examiner

*Primary Examiner* — Shafiqul Haq
(74) *Attorney, Agent, or Firm* — Hsiu-Ming Saunders; Intellectual Property Connections, Inc.

(57) ABSTRACT

The present invention provides methods, compositions, and systems for mass spectrometric analysis of magnetic nanoparticles displaying ligands on their surface. For example, the present invention provides methods of screening a sample for the presence of at least one analyte using ligand conjugated magnetic nanoparticles, magnetic separation, and mass spectrometric analysis. The present invention also relates to MALDI matrix compositions comprising ligand conjugated magnetic nanoparticles.

15 Claims, 13 Drawing Sheets

A

B

MASS SPECTROMETRIC ANALYSIS OF LIGAND CONJUGATED MAGNETIC NANOPARTICLES

The present application claims priority to U.S. Provisional Application Ser. No. 60/701,379 filed Jul. 21, 2005, which is herein incorporated by reference.

FIELD OF THE INVENTION

The present invention relates to methods, compositions, and systems for mass spectrometric analysis of ligand conjugated magnetic nanoparticles. For example, the present invention relates to methods of screening a sample for the presence of at least one analyte using ligand conjugated magnetic nanoparticles, magnetic separation, and mass spectrometric analysis. The present invention also relates to MALDI matrix compositions comprising ligand conjugated magnetic nanoparticles.

BACKGROUND OF THE INVENTION

The completion of human genome project has catalyzed advances in proteomics to investigate cellular function at the protein level. In particular, increasingly sophisticated techniques have been rapidly developed for discovering disease biomarkers via large-scale differential profiling. The recognition that every disease induces a specific pattern of change in proteomic microenvironments indicates important clinical implications on the early detection and progression of disease. Although plasma, urine, and saliva are readily available samples whose protein content reflects the environment encountered by the blood during its journey through tissues and the circulatory system, the body fluid-derived proteomes are complex, with a wide and dynamic range in protein abundance that imposes extreme analytical difficulties for medical studies or clinical diagnoses. With the advent of a growing number of candidate protein biomarkers for disease diagnosis, the development of sensitive techniques with great potential to monitor disease onset is urgently needed for the next phase of targeted proteomics.

The detection and diagnosis of disease in the clinical setting primarily depends on immunoassays based on antibody-antigen interactions. The most widely used of all the methods, enzyme-linked immunosorbent assay (ELISA), offers both specificity and sensitivity. Alternatively, protein chip-based approaches are increasingly used in clinical diagnosis, because the array format can be easily adapted to miniaturization, multiplexing and high-throughput. However, these traditional immunological methods are inconvenient and time-consuming because enzymes or fluorescent reagents have to be labeled. Fluorescence measurements also may have high background, leading to false positives, and produce photobleaching, leading to false negatives (see, e.g., Graham et al., Trends Biotechnol., 2004, 22:455-462, herein incorporated by reference).

Recent developments in mass spectrometry have greatly expanded the possibility of characterizing unknown proteins in proteomic research. Mass spectrometry is especially suitable for the direct detection of proteins, which enhances specificity without the use of fluorescent or radioactive labels. This approach offers greater flexibility in the selection of bioactive probes. Among these developments, matrix-assisted laser desorption/ionization time-of-flight mass spectrometry (MALDI-TOF MS) has become one of the primary techniques for protein identification due to its high sensitivity, tolerance to impurities, and high speed. Despite these advantages, the simultaneous characterization of hundreds to thousands of proteins in complex media still remains a challenge due to the suppression effect (see Wulfkuhle et al., Nat. Rev. Cancer, 2003, 3:267-275, herein incorporated by reference). Recently, surface-enhanced laser desorption/ionization (SELDI), has evolved rapidly as a new frontier for biomarker discovery and clinical diagnoses based on proteomic pattern analysis (see, Petricoin et al., Proteome Res. 2004, 3:209-217, herein incorporated by reference). Despite its advantages of high sensitivity and high throughput, the pattern recognition platform unfortunately suffers from laboratory-to-laboratory variance due to differences in sample handling and analysis software (see, Diamandis et al., Mol. Cell. Proteomics, 2004, 3:367-378, herein incorporated by reference).

As an alternative to the above approaches, MALDI MS can be combined with a biologically active probe to rapidly and specifically target proteins of interest. This targeted approach can accelerate research for class-specific proteins or biomarkers (Bundy et al., 2001, 73:751-757; Min et al., Nat. Biotechnol., 2004, 22:717-723; Warren et al., Anal. Chem., 2004, 76:4082-4092; and Zhang et al., Angew. Chem. Int. Ed., 2005, 44:615-617; all of which are herein incorporated by reference). Several analytical affinity capture techniques have been developed in the field of biological mass spectrometry. The research group of Hutchens et al. was one of the first to demonstrate MS-based affinity capture by immobilization of "bait" DNA on agarose beads for direct MALDI MS analysis of targeted proteins from complex biofluids (Hutchen et al., Mass Spectrom 1993, 7:576-580, herein incorporated by reference). The concept was further tailored by Nelson and coworkers to develop a mass spectrometric immunoassay (MSIA) (Nelson et al., Anal. Chem. 1995, 67:1153-1158, herein incorporated by reference). They used affinity pipette tips to selectively retrieve proteins from biological solutions, demonstrating high-throughput quantitative protein analysis as well as screening of heterogeneous glycan structures in plasma proteins (Nedelkow et al., Anal. Chem., 2004, 76:1733-1737; and Kiernan et al., Proteomics, 2004, 4:1825-1829, both of which are herein incorporated by reference). Variations of the biologically active probes for affinity mass spectrometry include the assay of direct desorption/ionization on silicon (DIOS) (Wei et al., Nature, 1999, 399:243-246, and Zou et al., Angew. Chem. Int. Ed. 2002, 41:646-648, both of which are herein incorporated by reference) and self-assembled monolayers (SAMs) (Brockman et al., Anal. Chem. 1995, 67, 4581-4585; and Su et al., Angew. Chem. Int. Ed. 2002, 41:4715-4718, both of which are herein incorporated by reference). Despite the rapid evolution of efficient chip-based or microbead-based assays for biomedical research, protein chip technologies face two main technical challenges. First, the physical and chemical properties of the chip surface may denature/alter the native three-dimensional structure of proteins, raising the possibility of disrupted bait-target protein interactions. Secondly, the requirement of specialized immobilization chemistry for surface engineering and/or specialized instruments limit the general application of these protein assay technologies in the general scientific community. Therefore, what is needed is a detection assay and associated compositions that avoid these problems.

SUMMARY OF THE INVENTION

The present invention provides methods, compositions, and systems for mass spectrometric analysis of ligand conjugated magnetic nanoparticles. For example, the present invention provides methods of screening a sample for the presence of at least one analyte using ligand conjugated magnetic nanoparticles, magnetic separation, and mass spectrometric analysis. The present invention also relates to MALDI matrix compositions comprising ligand conjugated magnetic nanoparticles.

In some embodiments, the present invention provides methods of screening a sample comprising; a) providing; i) a first population of magnetic nanoparticles, wherein the magnetic nanoparticles display (e.g., are conjugated to) a plurality of ligand molecules, and ii) a sample (e.g. biological sample) suspected of containing at least one type of target analyte; and b) mixing the first population of magnetic nanoparticles with the sample; c) separating (e.g., magnetically separating) at least a portion of the first population of magnetic nanoparticles from the sample thereby generating a second population of magnetic nanoparticles, and d) subjecting at least a portion of the second population of magnetic nanoparticles to mass spectrometric analysis under conditions such that the presence or absence of the at least one analyte in the sample is detected.

In certain embodiments, the methods further comprise a step after step c), but before step d), of washing and/or eluting the second population of magnetic nanoparticles. In other embodiments, at least a portion of the second population is mixed with matrix material, wherein the matrix material is configured for use in matrix assisted laser desorption-ionization (MALDI) mass spectrometry (e.g. MALDI-TOF or similar techniques). In particular embodiments, the mass spectrometric analysis comprises matrix assisted laser desorption-ionization (MALDI) mass spectrometry or similar type of mass spectrometry. In other embodiments, the mass spectrometric analysis comprises time of flight matrix assisted laser desorption-ionization (MALDI-TOF) mass spectrometry or similar method.

In particular embodiments, the presence of the analyte is detected and the mass spectrometric analysis determines an approximate amount of the at least one analyte in the sample (e.g., the method is quantitative or semi-quantitative). In some embodiments, the mass spectrometric analysis is multiplexed and detects the presence of at least two types of analytes (e.g. 2, 5, 10, 50, 100, or 1000 different types of analytes are detected). In some embodiments, the first population of magnetic nanoparticles comprises a first sub-population conjugated to ligands specific for one type of analyte and a second sub-population conjugated to ligands specific for a second type of analyte. In other embodiments, the first population of magnetic nanoparticles comprises a first, second, third, fourth, fifth, sixth . . . one-hundredth sub-population conjugated to a unique ligand specific for a particular analyte. In additional embodiments, the plurality of ligand molecules comprise at least two different types of ligand molecules (e.g. such that each magnetic nanoparticle is able to bind with two types of target analytes). In certain embodiments, the plurality of ligand molecules comprise at least three, four, five . . . one-hundred different types of ligand molecules (e.g. such that each magnetic nanoparticle is able to bind with three, four, five, etc. types of target analytes).

In particular embodiments, the at least one analyte is present in the sample at a concentration equal to or less than $1 \times 10^{-7}$ M, and wherein the presence of the at least one analyte is detected. In some embodiments, the at least one analyte is present in the sample at a concentration equal to or less than $1 \times 10^{-8}$ M or $1 \times 10^{-9}$ M (or between $1 \times 10^{-6}$ M and $1 \times 10^{-10}$ M or between $1 \times 10^{-7}$ M and $1 \times 10^{-9}$ M) and the presence of the at least one analyte is detected. In additional embodiments, the total volume of the sample is less than 10 µl. In further embodiments, the total volume of the sample is between 0.5 µl and 10 µl. In some embodiments, the total weight of the first population of magnetic nanoparticles is equal to or less than 10 µg (e.g. 10, 8, 6 or 4 µg). In further embodiments, the total weight of the first population of magnetic nanoparticles is between 10 µg and 5 µg. In certain embodiments, the sample comprises blood plasma. In other embodiments, the sample comprises fluid obtained from a subject (e.g. urine, blood, blood plasma, semen, stool, or any other type of fluid from a subject).

In some embodiments, the present invention provides compositions comprising; a) a population of magnetic nanoparticles, wherein the magnetic nanoparticles display (e.g., are conjugated to) a plurality of ligand molecules; and b) matrix material, wherein the matrix material is configured for use in mass spectrometric analysis (e.g., in matrix assisted laser desorption-ionization (MALDI) mass spectrometry). In certain embodiments, at least a portion of the ligands are bound to analyte molecules.

In particular embodiments, the present invention provides systems comprising; a) a population of magnetic nanoparticles, wherein the magnetic nanoparticles display (e.g., are conjugated to) a plurality of ligand molecules; and b) a mass spectrometric device, wherein the mass spectrometric device is configured to detect the presence or absence of at least one type of analyte bound to the ligand molecules. In certain embodiments, the mass spectrometric device is configured for matrix assisted laser desorption-ionization (MALDI) mass spectrometry. In some embodiments, the mass spectrometric device is configured for time of flight matrix assisted laser desorption-ionization (MALDI-TOF) mass spectrometry.

In certain embodiments, the plurality of ligand molecules comprises antibodies or antibody fragments. In further embodiments, the plurality of ligand molecules comprise proteins (e.g. receptors, antibodies, antibody fragments, etc), carbohydrate molecules, or nucleic acids (e.g. nucleic acids that are known to bind proteins, or nucleic acids found by methods such as the SELEX method). In some embodiments, the magnetic nanoparticles comprise blocking molecules (e.g. BSA, polyethylene glycol, methoxy polyethylene glycol, etc.). In other embodiments, the plurality of ligand molecules are conjugated to the magnetic nanoparticles via a linker molecule. (e.g. as shown in FIG. 1 and FIG. 9).

In particular embodiments, the matrix material has a pH of 2.0 or less (e.g. a pH of 2.0, 1.9, 1.8, 1.7, 1.6, 1.5, 1.3, 1.1, or 1.0). In further embodiments, the matrix material is selected from the group consisting of: nicotinic acid; glycerol; sinapinic acid; ferulic acid; caffeic acid; succinic acid; 2,5-dihydroxy benzoic acid; α-cyano-4-hydroxy cinnamic acid; 3-hydroxypicolinic acid, 2-(4-hydroxyphenylazo)-benzoic acid; 2,4,6-trihydroxy-acetophenone; 3-amino-4-hydroxy benzoic acid; 5-methoxysalicylic acid; 1-hydroxy isoquinoline; 2,6-dihydroxyacetophenone, 4-hydroxy-3-methoxyphenylpyruvic acid; indole-3-pyruvic acid; harmaline; 3-aminoquinilone; and compositions similar to any of these compounds.

In certain embodiments, the magnetic nanoparticles comprise a metallic core particle. In other embodiments, the metallic core particle has a diameter of 1 to 150 nanometers. In some embodiments, the metallic core particle has a diameter of 5 to 15 nanometers. In further embodiments, the metallic core particle has a diameter of 0.1 to 500 nanometers (e.g., 0.1 nm, 0.5 nm, 1.0 nm, 2 nm, 2.5 nm, 3 nm, 4 nm, 5 nm, 6 nm, 7 nm, 8 nm, 9 nm, 10 nm, 11 nm, 12 nm, 13 nm, 14 nm, 15 nm, 18 nm, 20 nm, 25 nm, 50 nm, 75 nm, 100 nm, 150 mm, 200 nm, 250 nm, 300 nm, 400 nm and 500 nm). In particular embodiments, the metallic core particle comprises a silicon coating. In some embodiments, the metallic core particle comprise iron (e.g., $Fe_3O_4$). In certain embodiments, the metallic core particle comprises a material selected from iron, nickel, cobalt, and alloy of these metals. In some embodiments, the magnetic nanoparticles comprise a ceramic core particle, wherein the core ceramic core particle has magnetic properties. In preferred embodiments, the magnetic nanoparticles comprise a core particle that exhibit superparamagnetic properties.

In some embodiments, the present invention provides kits comprising i) a population of magnetic nanoparticles, wherein the magnetic nanoparticles are conjugated to a plurality of ligand molecules, and ii) instructions for using the magnetic nanoparticles with mass spectrometric devices (e.g. instructions for therapeutic, diagnostics, or basic research use of the magnetic nanoparticles with mass spectrometric devices).

One feature of the screening methods of the present invention is the advantage of on-probe identification of unknown target proteins (or other molecules) by mass spectrometry or identifying binding epitopes on target analytes. In some embodiments, the present invention provides methods of screening a sample for target ligand binding molecules comprising; a) providing; i) a first population of magnetic nanoparticles, wherein the magnetic nanoparticles display (e.g., are conjugated to) a plurality of ligand molecules, and ii) a sample (e.g. biological sample) comprising candidate ligand binding molecules; and b) mixing the first population of magnetic nanoparticles with the sample under conditions such that at least one type of target ligand binding molecule binds to the ligand molecules; c) separating (e.g., magnetically separating) at least a portion of the first population of magnetic nanoparticles from the sample thereby generating a second population of magnetic nanoparticles, and d) subjecting at least a portion of the second population of magnetic nanoparticles to mass spectrometric analysis under conditions such that data regarding the at least one target ligand binding molecule is generated. In certain embodiments, the data comprises information on the mass of the at least one target ligand binding molecule. In other embodiments, the data comprises information on the mass of one or more fragments of the at least one target ligand binding molecule. In further embodiments, the target ligand binding molecule comprises a protein. In certain embodiments, the present invention provides methods of characterizing ligand molecule binding epitopes in a target molecule comprising; a) providing; i) a first population of magnetic nanoparticles, wherein the magnetic nanoparticles display a plurality of ligand molecules, and ii) a sample comprising candidate ligand binding molecules; and b) mixing the first population of magnetic nanoparticles with the sample under conditions such that at least one type of target ligand binding molecule binds to the ligand molecules; c) exposing said first population of magnetic nanoparticles to a digestion agent; d) magnetically separating at least a portion of the first population of magnetic nanoparticles from the sample thereby generating a second population of magnetic nanoparticles, and e) subjecting at least a portion of the second population of magnetic nanoparticles to mass spectrometric analysis under conditions such that data regarding at least one ligand binding molecule epitope is generated.

The mass spectrometric data generated by the methods of the present invention can be used to determine the identity of the target ligand binding molecule, using, for example, the MS-Fit database search engine with 100% sequence coverage. Additional details on MS-Fit, as well as the software used for MS-FIT, can be found on the internet at MS fit at "http://" followed by "prospector.ucsf.edu." The data generated by the present invention can be used, for example, with MS-FIT or similar programs to identify target proteins or binding epitopes.

DEFINITIONS

Figure 1:
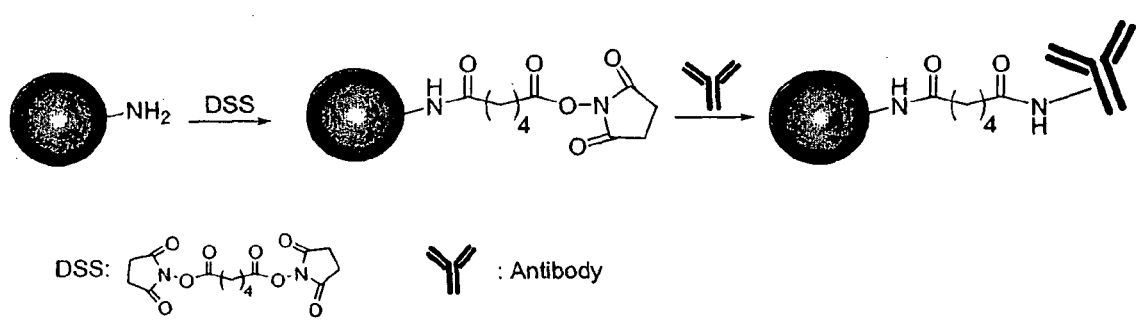
FIG. 1A shows one embodiment of the synthesis of an antibody conjugated magnetic nanoparticle.
FIG. 1B shows a nanoparticle size-distribution histogram of the particles having an average diameter of 10 nm.
Figure 1:
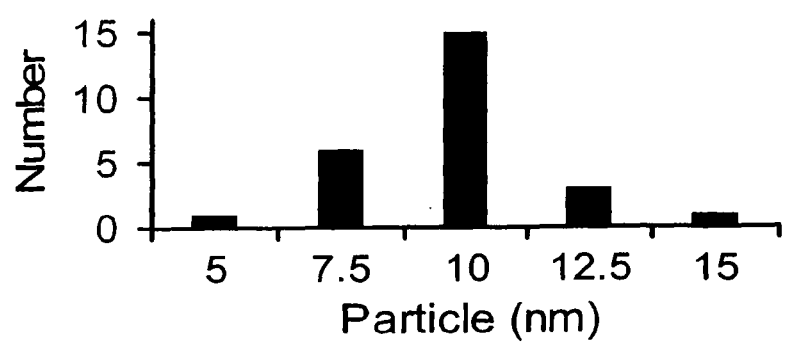

To facilitate an understanding of the invention, a number of terms are defined below.

As used herein, the terms "subject" and "patient" refer to any animal, such as a mammal like a dog, cat, bird, livestock (e.g. pig), and preferably a human.

The term "sample" in the present specification and claims is used in its broadest sense. On the one hand it is meant to include a specimen or culture (e.g., microbiological cultures). On the other hand, it is meant to include both biological and environmental samples (e.g., blood plasma sample). A sample may include a specimen of synthetic origin.

Biological samples may be animal, including human, fluid, solid (e.g., plasma) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

As used herein, the term "magnetic nanoparticle" refers to small particles (e.g. nanometer range) that are magnetic and effectively serve as a solid support or solid phase for conjugation to a ligand molecules. Even though particles can be of any size, the preferred size is 0.1-500 nanometers, preferably 1-150 nanometers, more preferably 5-15 nanometers, and most preferably about 9.0-10.0 nanometers. The particles may be uniform (e.g., being about the same size) or of variable size. Particles may be any shape (e.g. spherical or rod shaped), but are preferably made of regularly shaped material (e.g. spherical). The particles of the present invention are preferably composed of material that exhibits superparamagnetic properties (see, e.g., Spinu et al., IEEE Transactions on Magnetics, 36(5):3032-3034, 2000, herein incorporated by reference).

As used herein, the term "target analyte" refers to a molecule in a sample to be detected or targeted by magnetic nanoparticles. Examples of target molecules include, but are not limited to, cell surface ligands, cells in a subject, pathogens, such as bacteria and viruses, antibodies, naturally occurring drugs, synthetic drugs, pollutants, allergens, affector molecules, growth factors, chemokines, cytokines, and lymphokines. Preferably, the target analysts are found in blood plasma (e.g. human blood plasma).

The term "antibody," as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL.

As used herein, the term "antibody fragments" refers to a portion of an intact antibody. Examples of antibody fragments include, but are not limited to, linear antibodies, single-chain antibody molecules, Fab and $F(ab')_2$ fragments, and multispecific antibodies formed from antibody fragments. The antibody fragments preferably retain at least part of the heavy and/or light chain variable region.

As used herein, the phrase "matrix material" refers to material used to embed compounds to be analyzed by matrix assisted type mass spectrometric analysis (e.g. MALDI-TOF). Matrix material may be, for example, an organic acid with a strong absorption at the wavelength of the laser being used as part of mass spectrometric analysis.

As used herein, the terms "ligand" and "ligand molecule" refer to any molecule that is able to bind to another molecule (e.g. a target analyte). Preferably, the ligand molecules of the present invention are displayed on the surface of a magnetic nanoparticle (e.g. covalently attached via a linker to a magnetic nanoparticle). Example of ligand molecules include, but are not limited to, proteins (e.g. antibodies, antibody fragments or receptors), carbohydrates, lipids, or nucleic acids.

As used herein, the phrase "mass spectrometric analysis" refers to any method for identifying chemical composition of substances by use of a mass spectrometer, where a mass spectometer is a device that use magnetic fields, electric fields, or both to determine the masses of isotopes in a sample by producing a mass spectrum.

DESCRIPTION OF THE INVENTION

The present invention provides methods, compositions, and systems for mass spectrometric analysis of magnetic nanoparticles displaying ligand molecules. For example, the present invention provides methods of screening a sample for the presence of at least one analyte using ligand conjugated magnetic nanoparticles, magnetic separation, and mass spectrometric analysis. The present invention also relates to MALDI matrix compositions comprising ligand conjugated magnetic nanoparticles.

The ligand conjugated magnetic nanoparticles (mNPs) of the present invention, particularly antibody conjugated magnetic nanoparticles, are well suited for use with mass spectrometric analysis of biological samples (e.g. screening plasma samples). For example, as described in the Examples section, the present inventors have shown that covalent conjugation of antibodies to mNPs yields a stable affinity probe for mass spectrometric analysis (e.g. immunoassay), providing, for example, simultaneous isolation and pre-concentration of targeted proteins from un-fractionated human plasma. Mass spectrometric detection allows, for example, not only protein profiling but also screening of glycan structure microheterogeneity of targeted antigens. As shown in the Examples, assays with mNPs achieved subnanomolar ($10^{-9}$-

$10^{-10}$ M) limits of detection and showed good extraction efficiency for plasma protein that was highly diluted (e.g. 500-fold). With this level of sensitivity, the two exemplary proteins in human plasma targeted in the Examples could be analyzed unambiguously. This indicates that the mNPs+mass spectrometry approach of the present invention can be used to rapidly screen relatively low-level targeted proteins in complex mixtures containing other high-abundance proteins such as serum albumin. Compared with commercially available microscale particles, the antibody-conjugated mNPs of the present invention exhibited significantly better extraction efficiency and specificity.

The advantages of the mNP plus mass spectrometry approach of the present invention are numerous. For example, manufacturing costs for each assay (e.g. screening a plasma sample) may be low. Another advantage is that a user may be able to complete an assay in less than about 20 minutes. Another advantage is the ability to use the assays of the present invention in a high-throughput nanoarray format. A further advantage of many embodiments of the present invention is the ability to use as little as 1 μL of plasma from healthy individuals or patients to generate a target analyte profile.

The remainder of the description of the invention is provided below in the following sections: I. Magnetic Nanoparticles; II. Target Analytes and Ligand Molecules; and III. Mass Spectrometry with Ligand Conjugated Magnetic Nanoparticles.

I. Magnetic Nanoparticles

The magnetic nanoparticles of the present invention generally comprise a solid support magnetic core particle in the nanometer size range. The core particle employed to construct the ligand conjugated magnetic nanoparticles of the present invention are preferably small particles (e.g. nanometer range) that effectively serve as a solid support or solid phase for conjugation to a plurality of ligand molecules and used in conjunction with mass spectrometric methods. Even though particles can be of any size, the preferred size is 0.1-500 nanometers, preferably 1-150 nanometers, more preferably 5-15 nanometers, and most preferably about 9.0 nanometers. The particles may be uniform (e.g., being about the same size) or of variable size. Particles may be any shape (e.g. spherical or rod shaped), but are preferably made of regularly shaped material (e.g. spherical). The particles of the present invention are preferably composed of material that exhibits superparamagnetic properties.

Magnetic nanoparticles may be composed of any type of material that exhibits magnetic properties. For example, the nanoparticles useful in the present invention may be composed of a metal, such as iron, nickel, cobalt, and alloys of these metals. In certain embodiments, the magnetic nanoparticles are composed of ceramic material. Preferably, the magnetic nanoparticles are composed of material exhibiting superparamagnetic properties (e.g. particles that can be magnetized with an external magnetic field but dispersed simultaneously once the magnet is removed).

II. Target Analyte and Ligand Molecules

The present invention is not limited by the type of ligand molecules conjugated to the magnetic nanoparticles, nor is the invention limited by the type of target analyte that is detected by the mass spectrometric analysis. The target analytes and ligand molecules, may be, for example, proteins (e.g. antibodies, antibody fragments or receptors), carbohydrates, lipids, or nucleic acids. Preferably, the target analyte or ligand molecule is a protein found in human blood plasma (see, e.g., Anderson et al., Molecular & Cellular Proteomics, 3:311-326, 2004, herein incorporated by reference, including supplemental material associated with this reference). Examples of proteins in human plasma are provided in Table 1.

TABLE 1

| Target Analyte or Ligand Molecules | Accession Number |
| --- | --- |
| 60-kDa heat shock protein, mitochondrial precursor (Hsp60) (60-kDa chaperonin) (CPN60) (Heat shock protein 60) (HSP-60) (mitochondrial matrix protein P1) (P60 lymphocyte protein) (hucha60) | P10809 |
| 70-kDa peroxisomal membrane protein homolog (internal fragment) | AAB27045 |
| Actin, cytoplasmic 1 (β-actin) | P02570 |
| Adiponectin precursor (30-kDa adipocyte complement-related protein) (ACRP30) (adipose most abundant gene transcript 1) (apm-1) (gelatin-binding protein) | Q15848 |
| Afamin precursor; α-albumin (*Homo sapiens*) | NP_001124 |
| α-1-acid glycoprotein 1 precursor (AGP 1) (orosomucoid 1) (OMD 1) | P02763 |
| α-1-antichymotrypsin precursor (ACT) | P01011 |
| α-1-antitrypsin precursor (α-1 protease inhibitor) (α-1-antiproteinase) (PRO0684/PRO2209) | P01009 |
| α-1B-glycoprotein precursor (α-1-B glycoprotein) | P04217 |
| α-2-antiplasmin precursor (α-2-plasmin inhibitor) (α-2-PI) (α-2-AP) | P08697 |
| α-2-HS-glycoprotein precursor (Fetuin-A) (α-2-Z-globulin) (Ba-α-2-glycoprotein) (PRO2743) | P02765 |
| α-2-macroglobulin precursor (α-2-M) | P01023 |
| AMBP protein precursor [contains α-1-microglobulin (protein HC) (complex-forming glycoprotein heterogeneous in charge) (α-1 microglycoprotein); inter-α-trypsin inhibitor light chain (ITI-LC) (bikunin) (HI-30)] | P02760 |
| Angiotensinogen precursor [contains angiotensin I (Ang I); angiotensin II (Ang II); angiotensin III (Ang III) (Des-Asp[1]-angiotensin II)] | P01019 |
| Antithrombin-III precursor (ATIII) (PRO0309) | P01008 |
| Apolipoprotein A-I precursor (Apo-AI) | P02647 |
| Apolipoprotein A-II precursor (Apo-AII) (apoa-II) | P02652 |
| Apolipoprotein A-IV precursor (Apo-AIV) | P06727 |
| Apolipoprotein B-100 precursor (Apo B-100) [contains: apolipoprotein B-48 (Apo B-48)] | P04114 |
| Apolipoprotein C-II precursor (Apo-CII) | P02655 |
| Apolipoprotein C-III precursor (Apo-CIII) | P02656 |
| Apolipoprotein D precursor (Apo-D) (apod) | P05090 |
| Apolipoprotein E precursor (Apo-E) | P02649 |
| Apolipoprotein F precursor (Apo-F) | Q13790 |

TABLE 1-continued

| Target Analyte or Ligand Molecules | Accession Number |
|---|---|
| Apolipoprotein L1 precursor (apolipoprotein L-I) (apolipoprotein L) (apol-I) (Apo-L) (apol) | O14791 |
| Apolipoprotein(a) precursor (EC 3.4.21.—) (Apo(a)) (Lp(a)) | P08519 |
| ATP synthase β chain, mitochondrial precursor (EC 3.6.3.14) | P06576 |
| Atrial natriuretic factor precursor (ANF) (atrial natriuretic peptide) (ANP) (prepronatriodilatin) [contains: cardiodilatin-related peptide (CDP)] | P01160 |
| β-2-glycoprotein I precursor (apolipoprotein H) (Apo-H) (B2GPI) (β(2)GPI) (activated protein C-binding protein) (APC inhibitor) | P02749 |
| β-2-microglobulin precursor | P01884 |
| Bullous pemphigoid antigen, human (fragment) | I39467 |
| C4b-binding protein αchain precursor (c4bp) (proline-rich protein) (PRP) | P04003 |
| C4b-binding protein β chain precursor | P20851 |
| Calgranulin A (Migration inhibitory factor-related protein 8) (MRP-8) (cystic fibrosis antigen) (CFAG) (P8) (leukocyte L1 complex light chain) (S100 calcium-binding protein A8) (calprotectin L1L subunit) | P05109 |
| Carbonic anhydrase I; carbonic dehydratase (*Homo sapiens*) | NP_001729 |
| Carboxypeptidase N 83-kDa chain (carboxypeptidase N regulatory subunit) (fragment) | P22792 |
| Carboxypeptidase N catalytic chain precursor (EC 3.4.17.3) (arginine carboxypeptidase) (kinase 1) (serum carboxypeptidase N) (SCPN) (anaphylatoxin inactivator) (plasma carboxypeptidase B) | P15169 |
| Cathepsin D precursor (EC 3.4.23.5) | P07339 |
| Cathepsin L precursor (EC 3.4.22.15) (major excreted protein) (MEP) | P07711 |
| Cathepsin S precursor (EC 3.4.22.27) | P25774 |
| CCAAT/enhancer binding protein β, interleukin 6-dependent | NP_005185 |
| CD5 antigen-like precursor (SP-α) (CT-2) (igm-associated peptide) | O43866 |
| Centromere protein F (350/400 kd, mitosin); mitosin; centromere | NP_005187 |
| Ceruloplasmin precursor (EC 1.16.3.1) (ferroxidase) | P00450 |
| Chaperonin containing TCP1, subunit 4 (δ); chaperonin | NP_006421 |
| Chloride channel Ka; chloride channel, kidney, A; hclc-Ka (*Homo sapiens*) | NP_004061 |
| Cholinesterase precursor (EC 3.1.1.8) (acylcholine acylhydrolase) (choline esterase II) (butyrylcholine esterase) (pseudocholinesterase) | P06276 |
| Clusterin precursor (complement-associated protein SP-40, 40) (complement cytolysis inhibitor) (CLI) (NA1 and NA2) (apolipoprotein J) (Apo-J) (TRPM-2) | P10909 |
| Coagulation factor IX precursor (EC 3.4.21.22) (Christmas factor) | P00740 |
| Coagulation factor V precursor (activated protein C cofactor) | P12259 |
| Coagulation factor VIII precursor (procoagulant component) (antihemophilic factor) (AHF) | P00451 |
| Coagulation factor X precursor (EC 3.4.21.6) (Stuart factor) | P00742 |
| Coagulation factor XII precursor (EC 3.4.21.38) (Hageman factor) (HAF) | P00748 |
| Coagulation factor XIII A chain precursor (EC 2.3.2.13) (protein-glutamine γ-glutamyltransferase A chain) (transglutaminase A chain) | P00488 |
| Coagulation factor XIII B chain precursor (protein-glutamine γ-glutamyltransferase B chain) (transglutaminase B chain) (fibrin stabilizing factor B subunit) | P05160 |
| Collagen α1(IV) chain precursor | P02462 |
| Complement C1r component precursor | P00736 |
| Complement C1s component precursor (EC 3.4.21.42) (C1 esterase) | P09871 |
| Complement C2 precursor (EC 3.4.21.43) (C3/C5 convertase) | P06681 |
| Complement C3 precursor (contains C3a anaphylatoxin) | P01024 |
| Complement C4 precursor (contains C4A anaphylatoxin) | P01028 |
| Complement C5 precursor (contains C5a anaphylatoxin) | P01031 |
| Complement component C6 precursor | P13671 |
| Complement component C7 precursor | P10643 |
| Complement component C8 αchain precursor | P07357 |
| Complement component C8 β chain precursor | P07358 |
| Complement component C8 γchain precursor | P07360 |
| Complement component C9 precursor | P02748 |
| Complement factor B precursor (EC 3.4.21.47) (C3/C5 convertase) (properdin factor B) (glycine-rich β glycoprotein) (GBG) (PBF2) | P00751 |
| Complement factor H precursor (H factor 1) | P08603 |
| Complement factor H-related protein (clone H 36-1) precursor, human (fragment) | A40455 |
| Complement factor I precursor (EC 3.4.21.45) (C3B/C4B inactivator) | P05156 |
| Complement-activating component of Ra-reactive factor precursor (EC 3.4.21.—) (Ra-reactive factor serine protease p100) (rarf) (mannan-binding lectin serine protease 1) (mannose-binding protein associated serine protease) (MASP-1) | P48740 |
| Copper-transporting ATPase 1 (EC 3.6.3.4) (copper pump 1) (Menkes disease-associated protein) | Q04656 |
| Corticosteroid-binding globulin precursor (CBG) (transcortin) | P08185 |
| C-reactive protein precursor | P02741 |
| Creatine kinase, M chain (EC 2.7.3.2) (M-CK) | P06732 |
| Cytosolic purine 5′-nucleotidase (EC 3.1.3.5) | P49902 |
| D60S N-terminal lobe human lactoferrin | 1DSN |
| Dopamine β-monooxygenase precursor (EC 1.14.17.1) (dopamine β-hydroxylase) (DBH) | P09172 |
| Endothelin converting enzyme (EC 3.4.24.—) 1, umbilical vein endothelial cell form, human | JC2521 |
| Extracellular matrix protein 1 isoform 1 precursor; secretory | NP_004416 |
| Fibrinogen α/α-E chain precursor (contains fibrinopeptide A) | P02671 |
| Fibrinogen β chain precursor (contains fibrinopeptide B) | P02675 |

TABLE 1-continued

| Target Analyte or Ligand Molecules | Accession Number |
|---|---|
| Fibronectin precursor (FN) (cold-insoluble globulin) (CIG) | P02751 |
| Fibulin-1 precursor | P23142 |
| Ficolin 3 precursor (collagen/fibrinogen domain-containing protein 3) (collagen/fibrinogen domain-containing lectin 3 P35) (Hakata antigen) | O75636 |
| Follitropin β chain precursor (follicle-stimulating hormone β subunit) (FSH-β) (FSH-B) | P01225 |
| Gamma enolase (EC 4.2.1.11) (2-phospho-D-glycerate hydrolyase) (neural enolase) (NSE) (enolase 2) | P09104 |
| Gelsolin precursor, plasma (actin-depolymerizing factor) (ADF) (Brevin) (AGEL) | P06396 |
| Glial fibrillary acidic protein, astrocyte (GFAP) | P14136 |
| Glutamate carboxypeptidase II (EC 3.4.17.21) | Q04609 |
| Glutamyl aminopeptidase (EC 3.4.11.7), human | A47531 |
| Glycosylphosphatidylinositol specific phospholipase D1 isoform 1 | NP_001494 |
| GP120, IHRP = ITI heavy chain-related protein (internal fragment) | AAB34872 |
| Gravin, human | JW0057 |
| Haptoglobin-1 precursor | P00737 |
| Hemoglobin α chain | P01922 |
| Hemoglobin β chain | P02023 |
| Hemopexin precursor (β-1B-glycoprotein) | P02790 |
| Heparin cofactor II precursor (HC-II) (protease inhibitor leuserpin 2) (HLS2) | P05546 |
| Hepatocyte growth factor activator precursor (EC 3.4.21.—) (HGF activator) (HGFA) | Q04756 |
| HGF activator like protein (hyaluronan binding protein 2) | Q14520 |
| Histidine-rich glycoprotein precursor (histidine-proline rich glycoprotein) (HPRG) | P04196 |
| Human psoriasin (s100a7) | P31151 |
| Hypothetical protein dkfzp564a2416.1, human (fragment) | T14738 |
| Hypothetical protein dkfzp586m121.1, human (fragment) | T08772 |
| Hypothetical protein KIAA0437, human | T00063 |
| Immunoglobulin κ chain, human | S40354 |
| Immunoglobulin J chain | P01591 |
| Inhibin β A chain precursor (activin β-A chain) (erythroid differentiation protein) (EDF) | P08476 |
| Insulin-like growth factor binding protein 3 precursor (IGFBP-3) (IBP-3) (IGF-binding protein 3) | P17936 |
| Insulin-like growth factor binding protein 5 precursor (IGFBP-5) (IBP-5) (IGF-binding protein 5) | P24593 |
| Insulin-like growth factor binding protein complex acid labile chain precursor (ALS) | P35858 |
| Insulin-like growth factor IA precursor (IGF-IA) (somatomedin C) | P01343 |
| Inter-α-trypsin inhibitor heavy chain H1 precursor (ITI heavy chain H1) (Inter-α-inhibitor heavy chain 1) (Inter-α-trypsin inhibitor complex component III) (serum-derived hyaluronan-associated protein) (SHAP) | P19827 |
| Inter-α-trypsin inhibitor heavy chain H2 precursor (ITI heavy chain H2) (inter-α-inhibitor heavy chain 2) (inter-α-trypsin inhibitor complex component II) (serum-derived hyaluronan-associated protein) (SHAP) | P19823 |
| Inter-α-trypsin inhibitor heavy chain H3 precursor (ITI heavy chain H3) (Inter-α-inhibitor heavy chain 3) (serum-derived hyaluronan-associated protein) (SHAP) | Q06033 |
| Inter-α-trypsin inhibitor heavy chain H4 precursor | Q14624 |
| Interferon-induced viral resistance protein mxa, human | A33481 |
| Interleukin-12 α chain precursor (IL-12A) (cytotoxic lymphocyte maturation factor 35-kDa subunit) (CLMF p35) (NK cell stimulatory factor chain 1) (NKSF1) | P29459 |
| Interleukin-15 precursor (IL-15) | P40933 |
| Interleukin-6 precursor (IL-6) (B-cell stimulatory factor 2) (BSF-2) (interferon β-2) (hybridoma growth factor) | P05231 |
| Keratin 10, type I, cytoskeletal (clone HK51), human (fragment) | PC1102 |
| Kinesin family member 3A; kinesin family protein 3A (Homo sapiens) | NP_008985 |
| Kininogen precursor (α-2-thiol proteinase inhibitor) (contains bradykinin) | P01042 |
| Leucine-rich α-2-glycoprotein precursor (LRG) | P02750 |
| Lipopolysaccharide-binding protein precursor (LBP) | P18428 |
| L-lactate dehydrogenase B chain (EC 1.1.1.27) (LDH-B) (LDH heart subunit) (LDH-H) | P07195 |
| Lumican precursor (keratan sulfate proteoglycan lumican) (KSPG lumican) | P51884 |
| Melanoma-associated antigen p97 isoform 1, precursor | NP_005920 |
| Microtubule-associated protein τ (neurofibrillary tangle protein) (Paired helical filament-τ) (PHF-τ) | P10636 |
| Mismatch repair protein MSH2, human | I37550 |
| Mitotic kinesin-like protein-1 (kinesin-like protein 5) | Q02241 |
| Monocyte differentiation antigen CD14 precursor (myeloid cell-specific leucine-rich glycoprotein) | P08571 |
| Myosin heavy chain, nonmuscle type A (cellular myosin heavy chain, type A) (nonmuscle myosin heavy chain-A) (NMMHC-A) | P35579 |
| Myosin heavy chain, skeletal muscle, adult 1 (myosin heavy chain iix/d) (myhc-iix/d) | P12882 |
| Oxygen regulated protein precursor; oxygen regulated protein | NP_006380 |
| Parathyroid hormone precursor (Parathyrin) (PTH) (Parathormone) | P01270 |
| Peroxiredoxin 3; antioxidant protein 1; thioredoxin-dependent | NP_006784 |
| Peroxisome proliferator-activated receptor binding protein (PBP) (PPAR binding protein) (thyroid hormone receptor-associated protein complex component TRAP220) (thyroid receptor interacting protein 2) (TRIP2) (p53 regulatory protein RB18A) | Q15648 |
| Phosphatidylcholine-sterol acyltransferase precursor (EC 2.3.1.43) (lecithin-cholesterol acyltransferase) (phospholipid-cholesterol acyltransferase) | P04180 |
| Phosphodiesterase 5A isoform 1; cgmp-binding cgmp-specific | NP_001074 |

TABLE 1-continued

| Target Analyte or Ligand Molecules | Accession Number |
|---|---|
| Phosphoglycerate mutase 2 (EC 5.4.2.1) (EC 5.4.2.4) (EC 3.1.3.13) (phosphoglycerate mutase isozyme M) (PGAM-M) (BPG-dependent PGAM 2) (muscle-specific phosphoglycerate mutase) | P15259 |
| Phosphoinositide-3-kinase, catalytic, αpolypeptide | NP_006209 |
| Pigment epithelium-derived factor precursor (PEDF) (EPC-1) | P36955 |
| Plasma kallikrein precursor (EC 3.4.21.34) (plasma prekallikrein) (kininogenin) (Fletcher factor) | P03952 |
| Plasma protease C1 inhibitor precursor (C1 Inh) (C1 Inh) | P05155 |
| Plasma retinol-binding protein precursor (PRBP) (RBP) (PRO2222) | P02753 |
| Plasma serine protease inhibitor precursor (PCI) (protein C inhibitor) (plasminogen activator inhibitor-3) (PAI3) (acrosomal serine protease inhibitor) | P05154 |
| Plasminogen activator inhibitor-1 precursor (PAI-1) (endothelial plasminogen activator inhibitor) (PAI) | P05121 |
| Plasminogen precursor (EC 3.4.21.7) (contains angiostatin) | P00747 |
| Platelet basic protein precursor (PBP) (small inducible cytokine B7) (CXCL7) | P02775 |
| Platelet factor 4 precursor (PF-4) (CXCL4) (oncostatin A) (Iroplact) | P02776 |
| Platelet-activating factor acetylhydrolase IB αsubunit (EC 3.1.1.47) (PAF acetylhydrolase 45 kDa subunit) (PAF-AH 45-kDa subunit) (PAF-AH α) (PAFAH α) (Lissencephaly-1 protein) (LIS-1) | P43034 |
| Platelet-derived growth factor receptor αprecursor (*Homo sapiens*) | NP_006197 |
| Plectin 1, intermediate filament binding protein 500 kDa; plectin 1 | NP_000436 |
| Pregnancy zone protein precursor | P20742 |
| Prostate-specific antigen precursor (EC 3.4.21.77) (PSA) (γ-seminoprotein) (kallikrein 3) (semenogelase) (seminin) (P-30 antigen) | P07288 |
| Protein disulfide isomerase precursor (PDI) (EC 5.3.4.1) (prolyl 4-hydroxylase β subunit) (cellular thyroid hormone binding protein) (P55) | P07237 |
| Protein kinase, camp-dependent, regulatory, type I, α | NP_002725 |
| Protein tyrosine phosphatase; ptpase (*Homo sapiens*) | AAB22439 |
| Prothrombin precursor (EC 3.4.21.5) (coagulation factor II) | P00734 |
| Putative serum amyloid A-3 protein | P22614 |
| Receptor protein-tyrosine kinase erbb-2 precursor (EC 2.7.1.112) (p185erbb2) (NEU proto-oncogene) (C-erbb-2) (tyrosine kinase-type cell surface receptor HER2) (MLN 19) | P04626 |
| Rho-associated, coiled-coil containing protein kinase 1; p160rock | NP_005397 |
| Selenoprotein P precursor (sep) | P49908 |
| Serine (or cysteine) proteinase inhibitor, clade A (α-1) | NP_006206 |
| Serotransferrin precursor (transferrin) (siderophilin) (β-1-metal binding globulin) (PRO1400) | P02787 |
| Serum albumin precursor | P02768 |
| Serum amyloid A protein precursor (SAA) (contains amyloid protein A (amyloid fibril protein AA) | P02735 |
| Serum amyloid A-4 protein precursor (constitutively expressed serum amyloid A protein) (C-SAA) | P35542 |
| Serum amyloid P-component precursor (SAP) (9.5S α-1-glycoprotein) | P02743 |
| Serum paraoxonase/arylesterase 1 (EC 3.1.1.2) (EC 3.1.8.1) (PON 1) (serum aryldiakylphosphatase 1) (A-esterase 1) (aromatic esterase 1) (K-45) | P27169 |
| Sex hormone-binding globulin precursor (SHBG) (sex steroid-binding protein) (SBP) (testis-specific androgen-binding protein) (ABP) | P04278 |
| Signal recognition particle receptor αsubunit (SR-α) (docking protein α) (DP-α) | P08240 |
| Similar to human hsgcn1 U77700 (PID: g2282576); similar to yeast | AAC83183 |
| SPARC precursor (secreted protein acidic and rich in cysteine) (osteonectin) (ON) (basement membrane protein BM-40) | P09486 |
| Squamous cell carcinoma antigen 1 (SCCA-1) (protein T4-A) | P29508 |
| SWI/SNF-related matrix-associated actin-dependent regulator of | NP_003060 |
| Tetranectin precursor (TN) (plasminogen-kringle 4 binding protein) | P05452 |
| Thrombospondin 1 precursor | P07996 |
| Thyroglobulin precursor | P01266 |
| Thyroxine-binding globulin precursor (T4-binding globulin) | P05543 |
| Transthyretin precursor (prealbumin) (TBPA) (TTR) (ATTR) | P02766 |
| Trypsin 1 precursor (EC 3.4.21.4) (cationic trypsinogen) | P07477 |
| Vascular cell adhesion protein 1 precursor (V-CAM 1) (CD106 antigen) (INCAM-100) | P19320 |
| Vinculin (metavinculin) | P18206 |
| Vitamin D-binding protein precursor (DBP) (group-specific component) (GC-globulin) (VDB) | P02774 |
| Vitamin K-dependent protein S precursor | P07225 |
| Vitamin-K dependent protein C precursor (EC 3.4.21.69) (autoprothrombin IIA) (anticoagulant protein C) (blood coagulation factor XIV) | P04070 |
| Vitronectin precursor (serum spreading factor) (S-protein) (V75) (contains vitronectin V65 subunit; vitronectin V10 subunit; somatomedin B) | P04004 |
| V-kit Hardy-Zuckerman 4 feline sarcoma viral oncogene homolog | NP_000213 |
| Von Willebrand factor precursor (vwf) | P04275 |
| Zinc-α-2-glycoprotein precursor (Zn-α-2-glycoprotein) (Zn-α-2-GP) | P25311 |

In preferred embodiments, the magnetic nanoparticles are conjugated to antibodies or antibody fragments (e.g. antibodies or antibody fragments directed toward the molecules in Table 1). The antibodies and antibody fragments may be, for example, both polyclonal and monoclonal antibodies. Polyclonal antibodies may be raised, for example, in animals by multiple subcutaneous or intraperitoneal injections of the relevant antigen (e.g. proteins in Table 1) and an adjuvant. It may be useful to conjugate the relevant antigen to a protein that is immunogenic in the species to be immunized (e.g. keyhole limpet hemocyanin, serum albumin, bovine thyroglobulin, or soybean trypsin inhibitor) using a bifunctional or derivatizing agent. In some embodiments, monoclonal antibodies are conjugated to the magnetic nanoparticles of the present invention. Monoclonal antibodies may be made, for example, in a number of ways, including using the hybridoma method (e.g. as described by Kohler et al., Nature, 256: 495, 1975, herein incorporated by reference), or by recombinant DNA methods (e.g., U.S. Pat. No. 4,816,567, herein incorporated by reference).

In certain embodiments, the target analytes or ligand molecules are acute phase reactant molecules (or antibodies or antibody fragments thereto) found in plasma. The acute-phase response, the biosynthetic profiles of particular plasma proteins, involves the nonspecific physiological and biochemical responses of endothermic animals to most forms of tissue damage, infection, inflammation, and malignant neoplasia. In particular, the synthesis of a number of proteins is rapidly up-regulated, principally in hepatocytes, under the control of cytokines originating at the site of pathology. These proteins are termed acute-phase reactants (APRs) which have been divided into positive APR (one whose plasma concentration increases) and negative APR (one whose plasma concentration decreases). In mammals, typical positive APR including serum amyloid A protein (SAA), C-reactive protein (CRP) and serum amyloid P component (SAP) increases in plasma concentration in the magnitude between 50% to 1000-fold. The patterns of cytokine production and acute-phase response differ in different inflammatory conditions. Accordingly, acute-phase changes, as detected by the methods of the present invention, should reflect the presence and intensity of inflammation and therefore can be used as a clinical guide to diagnosis. As such, in some embodiments, the methods of the present invention are used to provide an APR plasma profile of a patient (e.g. to aid in the diagnosis or treatment of the patient).

In particular embodiments, the methods and compositions of the present invention are directed toward detecting the presence of absence of C-reactive protein (CRP). CRP belongs to the family of pentraxin which is named for its capacity to precipitate the somatic C-polysaccharide of *Streptococcus pneumonia*. The pentraxin family is highly conserved throughout nature and is known for its calcium-dependent ligand binding and lectin properties. CRP was one of the first acute-phase proteins to be described and is an exquisitely sensitive systemic marker of inflammation and tissue damage. CRP is the major APR in humans with mean concentration in human plasma is 0.8 mg/L. Following an acute-phase stimulus, the CRP level may increase as much as 10,000 fold (see, Pepys, et al., J. Exp. Clin. Invest, 2003, 111:1805-1812, herein incorporated by reference). CRP concentration is a useful non-specific biochemical marker of inflammation. As such, detecting CRP by the methods of the present invention allows, for example, one to (a) screen for organic disease, (b) monitor the response of treatment of inflammation and infection, and (c) detect intercurrent infection in diseases characterized by modest or absent acute-phase responses.

In certain embodiments, the methods and compositions of the present invention are directed toward detecting the presence of absence of serum amyloid P component (SAP). SAP is another member of the pentraxin family and is named for its universal presence in amyloid deposits such as Alzheimer's disease and the transmissible spongiform encephalopathies, where it is bound to amyloid fibrils. SAP is a pentameric glycoprotein in human plasma. SAP is non-acute phase protein in human and other species, but is the major APR in mice. SAP is highly resistant to proteolysis and its binding to amyloid fibrils is proposed to protect it from degradation and contribute to the presence of amyloid deposits, leading it to become the target of a new anti-Alzheimer's therapy (see, Pepys et al., Nature, 2002, 417:254-259, herein incorporated by reference).

III. Mass Spectrometry with Ligand Conjugated Magnetic Nanoparticles

Figure 9:
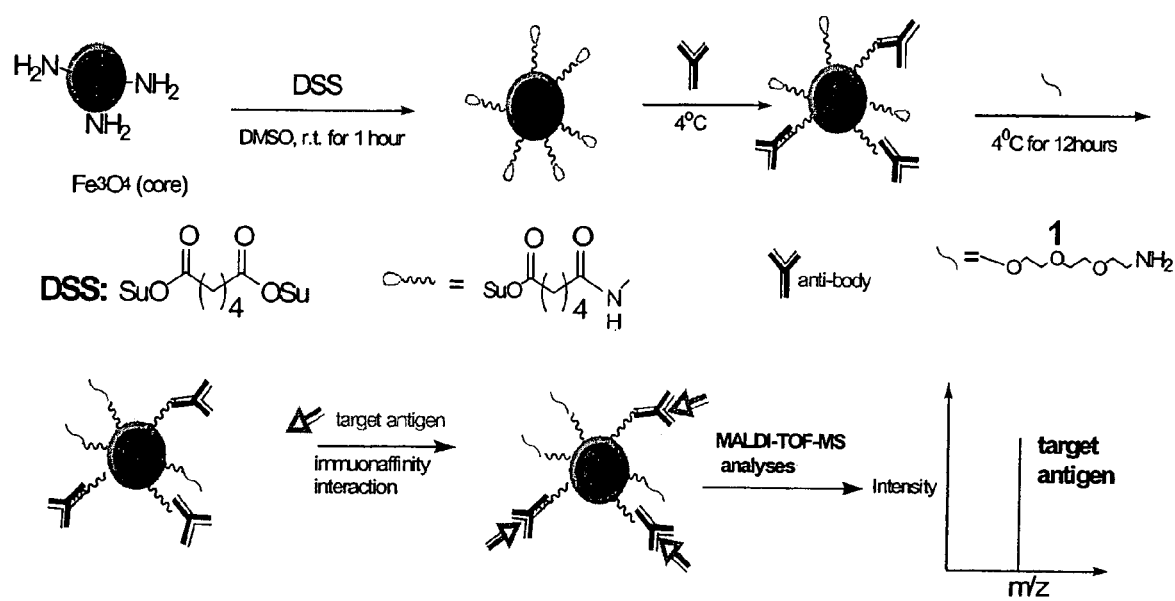
FIG. 9 shows one embodiment of the preparation of antibody-conjugated magnetic nanoparticles of the present invention and process for immunoaffinity assay.

The present invention provides methods of screening a sample for target analytes using ligand conjugated magnetic nanoparticles and mass spectrometry. FIG. 9 provides an exemplary embodiment of the methods of the present invention. As shown in this figure, a core $Fe_3O_4$ magnetic nanoparticle that is amino functionalized with a silicon coating is exposed to a linker molecule (DSS in this figure) to create a linker functionalized magnetic nanoparticle. This particle is then reacted with a plurality of ligand molecules (antibodies in FIG. 9) to create a ligand conjugated magnetic nanoparticle. Empty binding sites on this particle are then blocked with a blocking molecule (methoxy ethylene glycol is shown as an example in FIG. 9). This ligand conjugated magnetic nanoparticle is then exposed to a sample that contains a target analyte (target antigen in FIG. 9). The magnetic nanoparticle, with bound target analyte, may be mixed with MALDI-TOF matrix material (e.g. SA) and then subjected to mass spectrometric analysis (e.g. MALDI-TOF analysis is shown in FIG. 9). In this regard, the presence of the target analyte can be detected in the sample.

The present invention is not limited by the nature of the mass spectrometry technique utilized for analysis of the ligand conjugated magnetic nanoparticles. For example, techniques that find use with the present invention include, but are not limited to, ion trap mass spectrometry, ion trap/time-of-flight mass spectrometry, matrix assisted laser desorption/ionization (MALDI), MALDI-TOF, MALDI-TOF-TOF, quadrupole and triple quadrupole mass spectrometry, Fourier Transform (ICR) mass spectrometry, and magnetic sector mass spectrometry. Those skilled in the art will appreciate the applicability of other mass spectroscopic techniques to such methods.

In preferred embodiments, matrix assisted laser desorption/ionization (MALDI) type mass spectrometry is employed. MALDI mass spectrometry can be divided into two steps. The first step involves preparing a sample by mixing the ligand conjugated magnetic nanoparticles of the present invention, which may be bound to an target analyte, with a molar excess of matrix material. The matrix material is generally an organic acid with a strong absorption at the wavelength of the laser being used. The mixture is allowed to dry and the resultant nanoprobe-target complex is embedded in the matrix crystal. The second step generally involves desorption of bulk portions of the solid sample by intense pulses of laser light. The irradiation by the laser (typically 3-5 ns) induces rapid heating of the matrix crystals, resulting in localized sublimation of matrix/target protein (protein fragment) crystals, and entraining intact analyte into the expanding matrix plume. In preferred embodiments, MALDI mass spectrometry is combined with time of flight (TOF) analysis.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); 1 or L (liters); ml (milliliters); µl (microliters); cm (centimeters); mm (millimeters); µm (micrometers); nm (nanometers); DS (dextran sulfate); and C (degrees Centigrade).

Example 1

Mass Spectrometry Detection with Magnetic Nanoparticles Displaying Antibodies This example describes construction of various antibody displaying magnetic nanoparticles and their use to detect target analyte molecules in samples using mass spectrometry. In particular, this example describes the construction of magnetic nanoparticles conjugated with anti-SAP or anti-CRP antibodies and the use of these nanoparticles to detect SAP and CRP in biological samples using mass spectrometry.

Materials and Methods

Materials. Cytochrome c, myoglobin, enolase, and sinapinic acid (SA) were purchased from Sigma-Aldrich (Mississauga, ON, Canada). SAP and CRP were obtained from Calbiochem (San Diego, Calif., USA). Polyclonal anti-SAP was purchased from DakoCytomation (Carpinteria, Calif., USA). Monoclonal anti-CRP was purchased from Biodesign (Kennebunk, Me., USA). The magnetic Separator was from Qiagen (Valencia, Calif., USA).

Synthesis of Antibody-Conjugated Magnetic Nanoparticles. Iron oxide nanoparticles ($Fe_3O_4$) were synthesized by co-precipitation using $FeCl_2$ and $FeCl_3$ under basic conditions (see, Kang et al., Chem. Mater, 1996, 8:2209-2211, herein incorporated by reference). During preparation, the desired "core" mNPs were treated with tetraethyl orthosilicate (TEOS) to create the silica-coated surface. Subsequently, 3-aminopropyltrimethoxysilane (APS) was added for aminosilane modification to give mNPs.

The antibody of interest was covalently linked to the mNPs surface through the cross-linker bis(N-hydroxysuccinimide ester) (NHS-ester; DSS; see FIG. 1A). In brief, aminosilane-modified mNPs (0.5 mg) were dissolved in DMSO (0.5 mL) and immediately incubated with DSS solution for 1 hour at room temperature. This solution was then dried and resuspended with either anti-SAP solution (8.1 mg/mL, 25 µL) or anti-CRP solution (15.4 mg/mL, 15 µL). The mixture was incubated at 4° C. for overnight. The cross-linker is active for primary amines and thus can bridge between the aminosilane-modified mNPs and antibodies (or other proteins). Finally, the antibody-conjugated mNPs products were magnetically separated and extensively washed with PBS (0.1 M, pH 7.4) to remove excess reactants. The final product was dried and stored at 4° C. for further use.

To compare with magnetic microbeads, commercially available magnetic microbeads (Dynal Biotech, 2.8 µm) were conjugated with antibody as described above.

Immunoaffinity Capture of Antigens. For the protein pool experiments, 10 µg mNPs were immersed in 60 µL of PBS (pH 7.4), containing 0.5 µM myoglobin, 0.1 µM CRP, 0.67 µM SAP, and 2.1 µM enolase for 60 minutes at room temperature. Unbound proteins were removed by isolating the mNPs using a magnetic separator. The mNPs were then washed four times with 100 µL of 25 mM ammonium bicarbonate. For subsequent MALDI MS analysis, the mNPs were directly mixed with 1~2 µL MALDI matrix SA (10 mg sinapinic acid dissolved in 1 mL solution containing 50% acetonitrile, 50% water, and 0.1% trifluoroacetic acid), spotted onto the sample plate, air dried and analyzed. For human plasma analyses, aliquots (5-20 µL) of plasma, diluted in PBS (pH 7.4), were mixed with mNPs (conjugated with either anti-SAP or anti-CRP) and subjected to the same immunoaffinity reaction and MALDI MS analysis.

To evaluate the effect of incubation time, 1 µL aliquots of 50 µL (40 ng/µL SAP) samples from supernatant were immediately transferred to the sample plate at different times: 0, 3, 10, 30 and 60 min. Each sample was then applied with 0.5 µL MALDI matrix and subsequently analyzed by MALDI MS.

Mass Spectrometry. All mass spectra were acquired by using a MALDI-TOF mass spectrometer Voyager DE-STR (PerSeptive Biosystems, USA) equipped with a 337-nm nitrogen laser. The spectra were recorded in the linear mode using an accelerating voltage of 25 kV, a 90% grid voltage, 0.3% guide wire voltage, 650 ns delay time and a low-mass gate of 5000 Da. External mass calibration was usually applied based on a mixture of two reference proteins [cytochrome c (M.W.=12361) and myoglobin (M.W.=16952)] covering the m/z range of 5 kDa to 80 kDa. A typical mass spectrum was obtained by averaging 250 laser shots followed by noise reduction and Gaussian smoothing using Data-Explorer software (Applied Biosystems, Foster City, Calif., USA).

Plasma Samples. Plasma samples from four patients with gastric cancer and four healthy controls were obtained with informed consent from the Department of General Surgery, Tri-Services General Hospital, Taipei, Taiwan. The procedure was approved by the Review Boards of Tri-Service General Hospital, National Defense Medical Center. Plasma levels of CRP were measured by the latex-particle-enhanced immunonephelometric assay using a nephelometer (Dade Behring, Marburg, Germany) (Juan et al., Proteomics, 2004, 4:2766-2775, herein incorporated by reference). SAS 8.0 statistical software (SAS Institute GmbH, Heidelberg, Germany) was used for statistical analysis. The Wilcoxon rank sum test was used to compare CRP levels between healthy donors and patients with gastric cancer.

Preparation and Characterization of Nanoparticles

The synthesis of antibody-conjugated mNPs is illustrated in FIG. 1A. The superparamagnetic nanoparticles ($Fe_3O_4$) were synthesized as described above. Nanoprobe stability and specific activity are important parameters for the engineering of an optimal nanoparticle-antibody immunoassay. In order to develop more stable antibody-nanoparticle bioconjugates, the antibodies of interest (anti-SAP and anti-CRP) were covalently conjugated to the aminosilane-modified mNPs through the bifunctionally amine-active cross-linker (DSS) (see FIG. 1A). A transmission electron micrograph of the antibody-conjugated mNPs was obtained. Small particle size can reduce steric hindrance and thus improve specific activity. The size-distribution histogram of the mNPs (FIG. 1B) indicates that the diameter of iron oxide "core" ranges from 5-15 nm, with an average diameter of ~9.7 nm. In general, choosing particles below about 15 nm in diameter ensures their superparamagnetism, which allows stability and dispersion upon removal of the magnetic field (see, Tartaj et al, J. Phys. D. Appl. Phys, 2003, 36, R182-197, herein incorporated by reference). Approximately 46 µg (320 pmol) of anti-SAP was immobilized on the surface of 1.0 mg mNPs, as determined using the BCA protein assay. Similarly, ~9.8 µg (66 pmol) of monoclonal anti-CRP was immobilized.

These antibody-nanoparticle bioconjugates could be stored in PBS, pH 7.4, at 4° C. for at least six months without decomposition.

Protein Pool Experiments

Aliquots of functionalized mNPs were incubated with a biological medium containing the targeted antigen. After the immunoaffinity interaction, the antigen-nanoparticle complexes were separated using a magnet, and non-antigenic proteins and interfering impurities were subsequently removed by a series of washes, abrogating the need for purification and desalting. Finally, the nanoparticles were directly mixed with matrix for MALDI MS analyses. To mimic a complex biological medium, a protein pool was prepared in 60 μL PBS (0.01 M, pH 7.4) composed of antigenic proteins (SAP, 20% molar fraction and CRP, 3% molar fraction) and two other "non-antigenic" proteins, myoglobin (Myo, 15%) and enolase (Eno, 62%). The abundance of the antigenic proteins was purposely reduced to test the extraction efficiency of the targeted protein.

Figure 2:
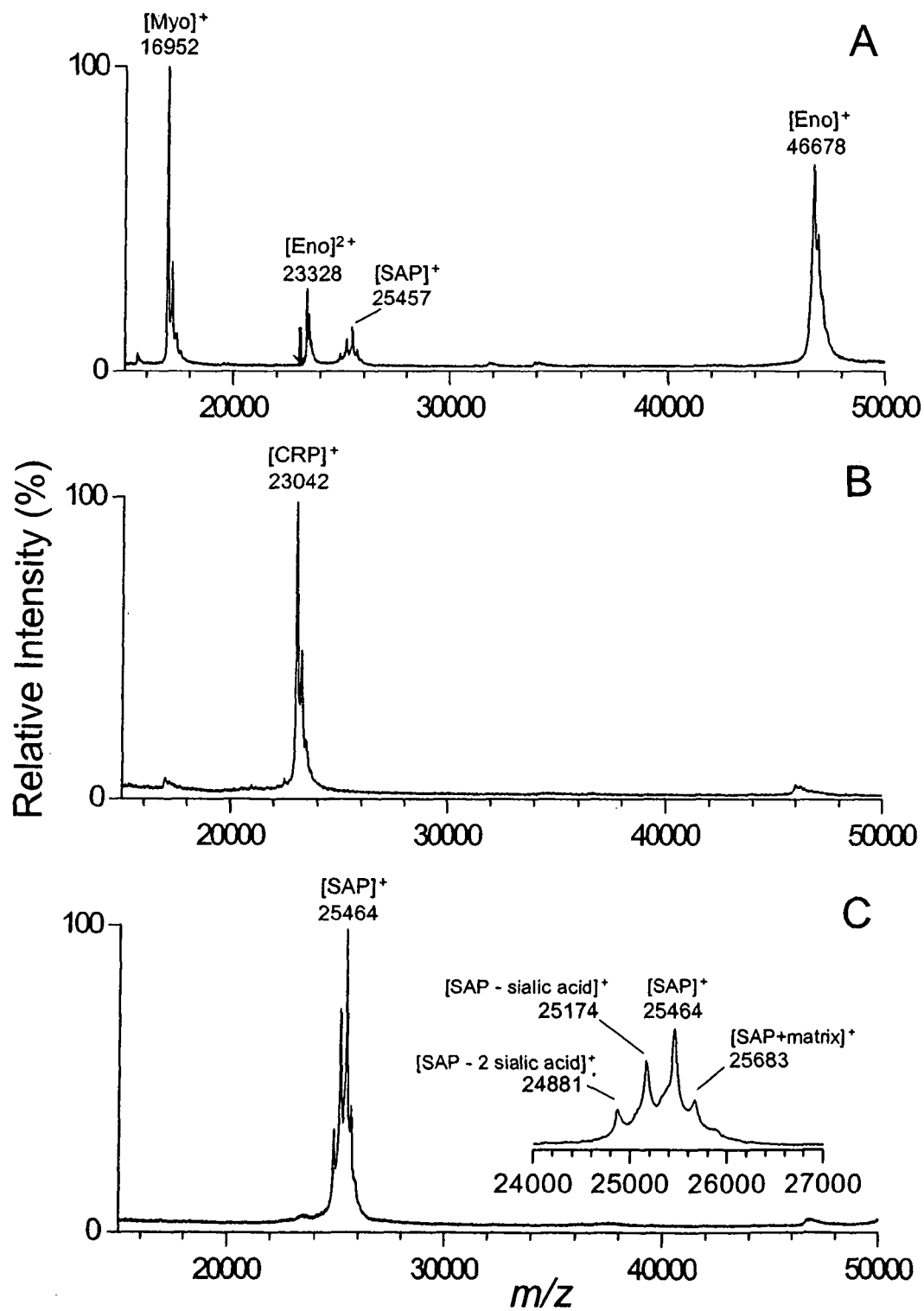
FIG. 2 shows a MALDI mass spectra of a protein mixture before (A) and after using (B) anti-CRP- or (C) anti-SAP-conjugated mNPs to extract a specific protein. The protein solution (60 µL) was composed of 0.5 µM myoglobin (Myo), 0.1 µM C-reactive protein (CRP), 0.67 µM serum amyloid P component (SAP), and 2.1 µM enolase (Eno). The arrow in the mass spectrum of (A) indicates the theoretical m/z of CRP. The inset of (C) shows detailed protein expression profiles of wild type, monosialo-, and asialo-SAP.

Prior to affinity extraction, as shown in FIG. 2A, the MALDI spectrum of the protein mixture shows the complexity of the mixture, in which the targeted antigen, CRP, was not observed due to its low abundance (3% molar fraction) and the ion suppression effect (see, Krause et al., Anal. Chem., 1999, 71:4160-4165, herein incorporated by reference). Suppression effects are commonly observed in MALDI MS due to the presence of salts, buffer or other more abundant species in complex biological media (see, Knochenmuss et al., Chem. Rev. 2003, 103, 441-452, herein incorporated by reference). The suppression effect can result in reduced signal intensity or even disappearance of the targeted analyte.

After affinity extraction, the MALDI spectrum in FIG. 2B reveals the specificity of nanoscale immunoassay, where CRP was selectively concentrated and detected with an excellent signal-to-noise ratio of 822. No background peak between m/z 5000-50000 was observed in control experiments before the addition of the protein mixture, showing no detectable "chemical noise" arising from the antibody-conjugated mNPs. The absence of other abundant proteins in FIG. 2B excluded nonspecific binding arising from electrostatic attraction or hydrogen bonding. The use of mNPs as a MALDI substrate overcomes the suppression effect because the particles are washed extensively to remove salt and abundant/non-antigenic proteins from the biological sample. The clean mass spectrum demonstrates the advantages of nanoprobe-based affinity extraction in providing simultaneous protein isolation, enrichment, and sample desalting without the necessity of additional elution steps. In general, antibody-antigen interactions are strong, having dissociation constants (Kd) ranging from $10^{-7}$ to $10^{-11}$ M. Most antibody-antigen complexes can be dissociated at extreme pH (i.e., pH<2 or pH>12). The pH of matrix solution (SA) is typically less than 2, and thus may serve to elute the antigen bound to the antibody-conjugated mNPs.

Mass spectrometric detection is also ideal for characterizing posttranslational modifications that cannot be predicted from genomic information. The MALDI spectrum in FIG. 2C shows a cluster of peaks corresponding to several SAP variants from the affinity extraction using anti-SAP-conjugated mNPs. The expanded view shows that mass spectrum is dominated by the mass of 25464±4 Da, consistent with the theoretical value of 25462 Da, as calculated from the known sequence. Accompanying the major peak were two peaks at 25174 Da and 24881 Da, corresponding to mass shifts of 290 Da and 583 Da, respectively. Within the experimental uncertainty, the shifts can be attributed to the loss of one or two sialic acid residues (each residue M.W.=291). In the linear mode, we found that the mass resolution did not deteriorate when the antigen-bound mNPs were deposited on the MALDI probe. Similarly, a mass accuracy of 0.02% could be routinely obtained by external calibration, comparable to the mass accuracy of conventional MALDI detection. Thus, the "direct" analysis of mNPs does not diminish the performance of the MALDI MS.

Kinetic Study of the Immunoreaction

Figure 3:
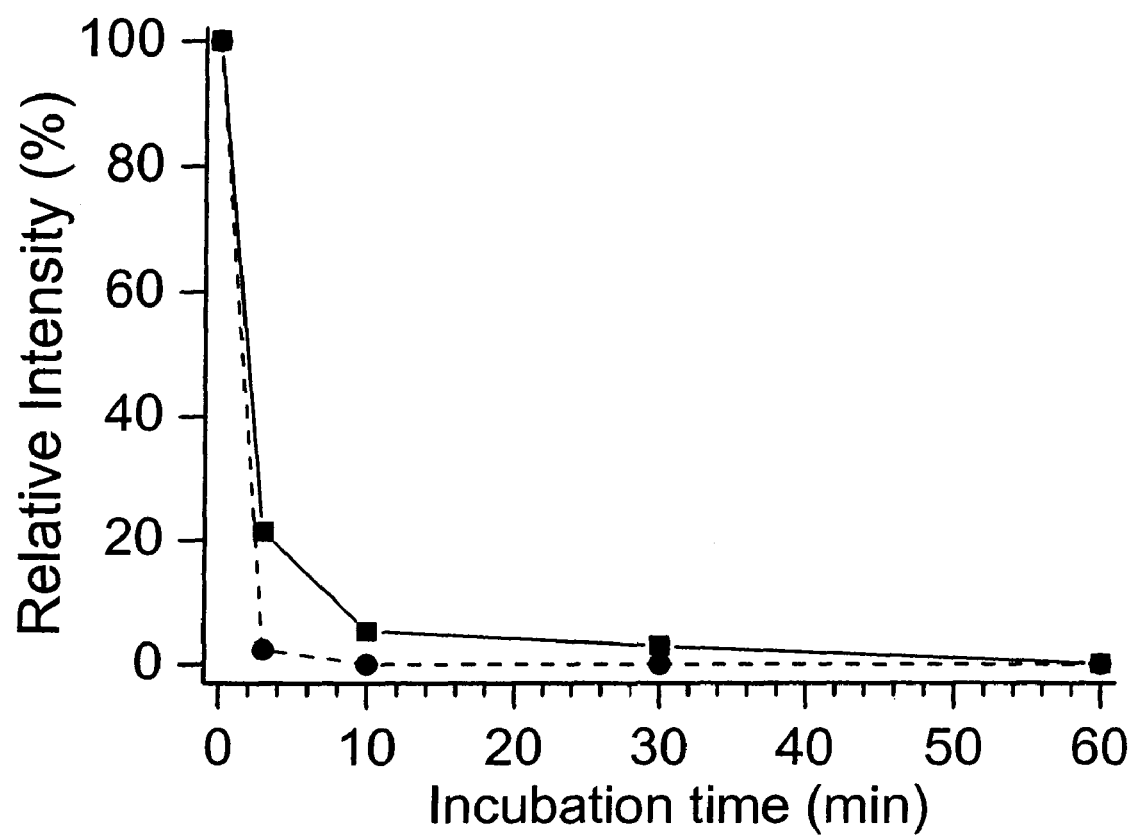
FIG. 3 shows the effect of incubation time on antibody-antigen recognition using antibody-conjugated mNPs. To investigate the time course of antibody-antigen recognition on mNPs, 1 µL of supernatant was sampled from a 60-µL reaction after different incubation times. The mNPs were conjugated with: anti-SAP (squares with solid line) and anti-CRP (circles with dashed line). After incubation (3 min to 1 hr), the quantities of the antigen remaining in the supernatant were detected by MALDI MS, and the peak intensities were plotted as a function of incubation time.

The use of antibody-conjugated mNPs significantly reduces sample handling time. In immunological assays, the incubation of antibody and antigen is often the rate-limiting step (e.g. 30 min to overnight for conventional ELISA) (see, e.g., Wang et al., J. Agric. Food Chem., 2004, 52:7793-7797, herein incorporated by reference). To evaluate the efficiency, the effect of incubation time on antibody-antigen recognition was investigated. After incubation of antibody-conjugated mNPs with antigen solution, the amount of remaining antigen was measured by MALDI MS. FIG. 3 shows that the peak intensities, corresponding to unbound antigen (SAP) in solution, decreased dramatically as a function of incubation time over 10 min, at which time free SAP was barely detectable (signal to noise ratio was <3). Significantly, maximum binding of CRP was almost completed in even shorter incubation time (<3 min).

This approach directly detected specific antibody-captured antigens by MALDI MS without using a secondary antibody or a reporter reaction. Unlike conventional immunoassays such as ELISA, for which the overall process usually requires at least 4 hours, our mNP-based immunoassay can be shortened within 15-20 minutes. Thus, this rapid and sensitive approach is amenable to clinical applications such as high-throughput or population screening.

Detection Sensitivity

Figure 4:
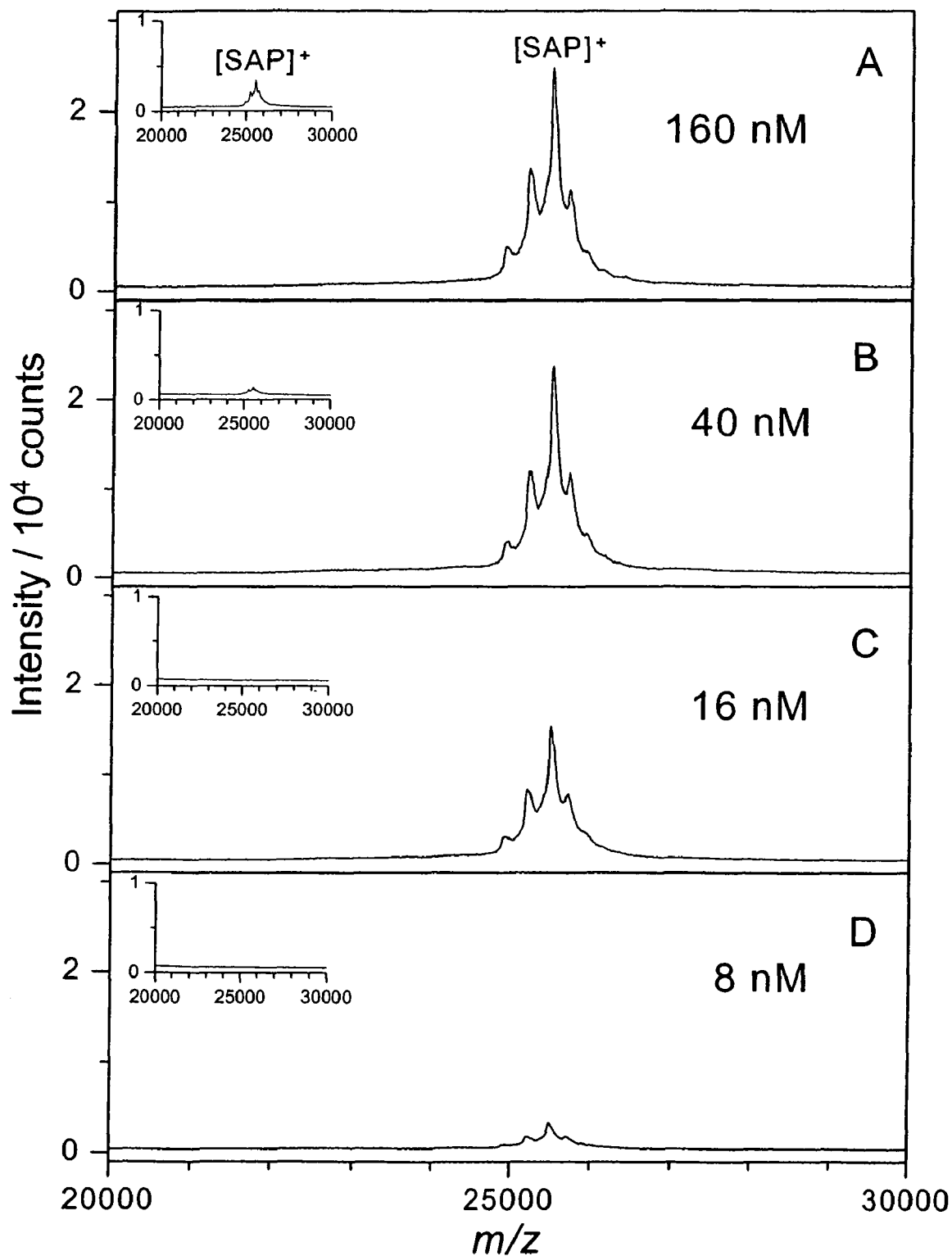
FIG. 4 shows a MALDI mass spectra of serum amyloid P component (SAP) extracted from diluted solution using anti-SAP-conjugated mNPs: (A) 160 nM SAP, 50 µL; (B) 40 nM, 200 µL; (C) 16 nM, 500 µL; (D) 8 nM, 1000 µL. The inset of each panel shows the mass spectrum of solution prior to extraction.

Another advantage of the nanoprobe-based immunoassay is the ability to preconcentrate the antigen from diluted medium to a small volume of mNPs. To demonstrate this concentration effect, a series of solutions with different SAP concentration (160 nM to 8 nM) were prepared by diluting an equal quantity (8 pmol) of SAP into different volumes. FIG. 4 shows the MALDI mass spectra of extracted SAP after preconcentration using anti-SAP-conjugated mNPs. By contrast, the SAP peak was barely discernable (or not detected) when the diluted samples were analyzed by conventional MALDI, as shown in the inset of each panel.

Figure 5:
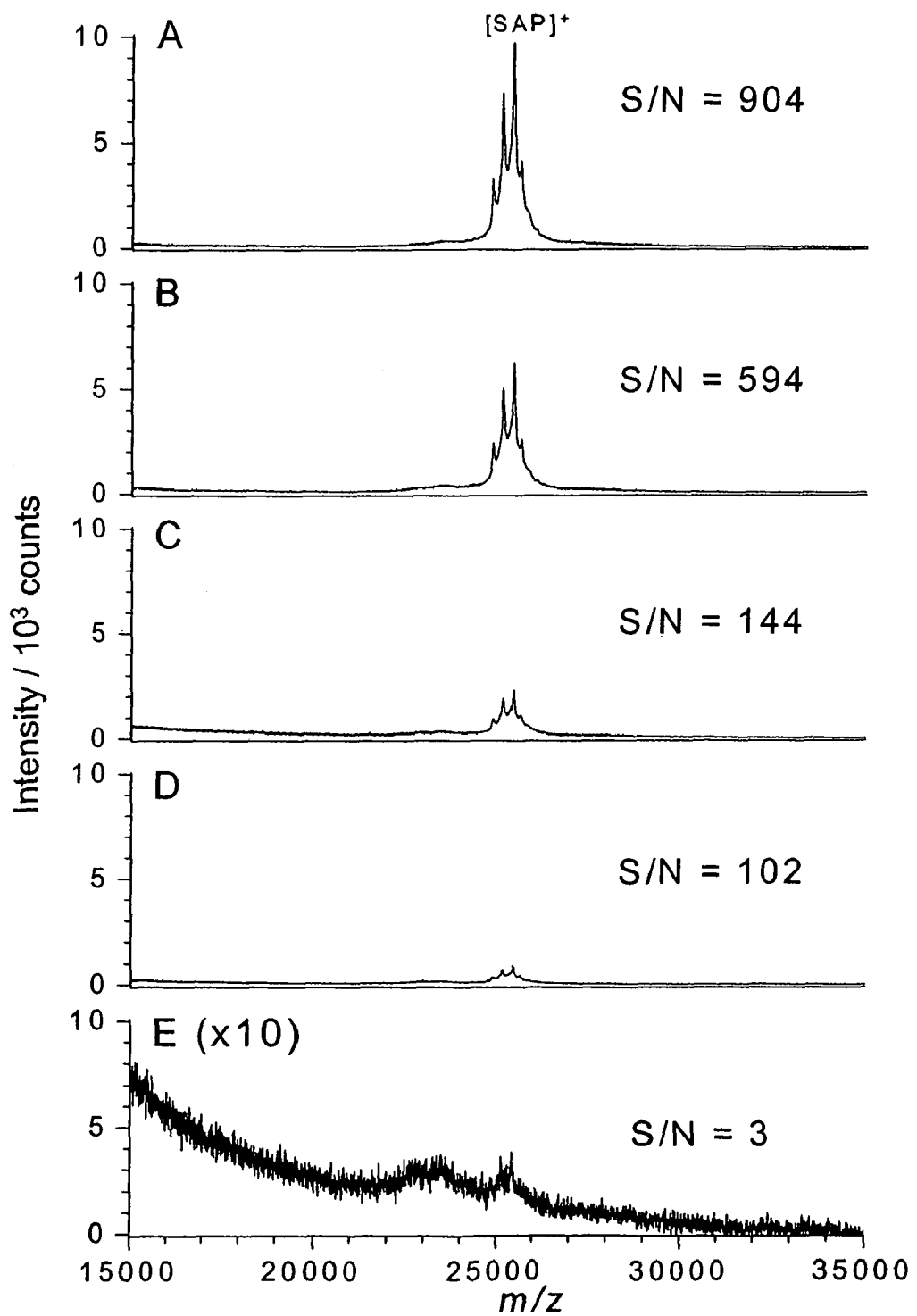
FIG. 5 shows the MALDI mass spectra of serum amyloid P component (SAP) extracted from 60 µL of protein solution of (A) 1.9 µM, (B) 80 nM, (C) 15 nM, (D) 3 nM, (E) 0.6 nM, using anti-SAP-conjugated mNPs.

The lower limit of detection, for this particular example, was explored using different amounts of SAP. After affinity extraction, FIG. 5 shows the mass spectra of 60 μL of SAP solution after a series of dilutions ranging from 54 μg/mL to 16 ng/mL (1.9 μM to 0.6 nM). The SAP signals decrease progressively with decreasing concentration. Strong peak intensities were observed in all spectra except that for the 0.6 nM solution, which had a signal-to-noise ratio of 3. Theoretically, the sensitivity of the current example depends on the MALDI MS detection sensitivity and the efficiency of affinity extraction. Assuming full recovery of all the SAP present in the 60 μL of diluted solution, the detection limit in this example is estimated to be 36 fmol, which is comparable to the detection limit by direct deposition of SAP onto the MALDI probe (data not shown). It is noteworthy that SAP and CRP levels in sera from healthy individuals were about 1.6 μM and 40 nM, respectively.

Detection of CRP and SAP from Human Plasma

It is well recognized that the human plasma proteomics holds the promise of both a revolution in disease diagnosis and therapeutic aspects. However, human plasma is a very complex mixture of proteins having a wide and dynamic range of abundance of more than $10^{12}$. Indeed, 22 proteins constitute about 99% of the protein content in plasma, with the remaining 1% comprising low-abundance proteins that are of great interest as potential biomarkers (see, e.g., Tirumalai et al., Mol. Cell Proteomics, 2003, 2:1096-1103, herein incorporated by reference). Thus, the magnetic nanoparticles of the present invention are preferably used to detect low level proteins in human plasma.

Figure 6:
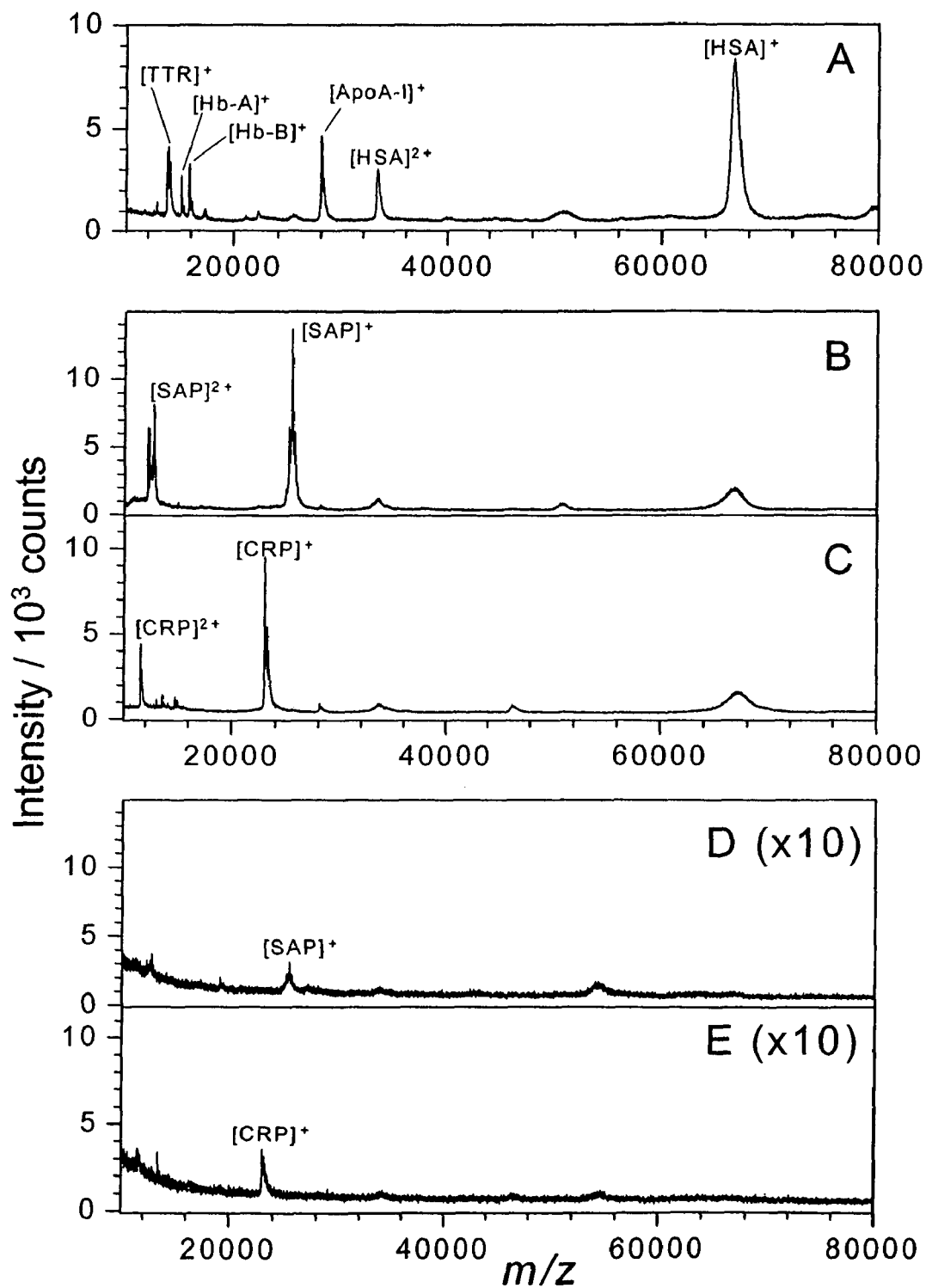
FIG. 6 shows a comparison of affinity extraction between antibody-conjugated magnetic nanoparticles and magnetic microbeads: (A) MALDI mass spectrum of 200-fold-diluted plasma; high-abundance proteins were so dominant that the signals from SAP or CRP were buried in the spectrum. Representative mass spectra of (B) SAP and (C) CRP were obtained after extraction using antibody-conjugated mNPs. Spectra for antibody-conjugated microbeads are shown in (D) SAP and (E) CRP.

To evaluate the specificity of the methods described in this example, 5 µL of plasma from a healthy subject was incubated sequentially with anti-SAP- and with anti-CRP-conjugated mNPs for affinity extraction of SAP and CRP, respectively. Prior to immunoaffinity extraction, no protein profile could be obtained from the stock plasma sample due to the interference of the salt and other plasma components. The plasma sample was therefore diluted 200-fold to reduce the salt concentration and subjected it to analysis. The protein profile in FIG. 6A shows the commonly observed abundant plasma proteins, including human serum albumin (HSA), apolipoprotein A-I (ApoA-I), hemoglobin alpha chain (Hb-A), hemoglobin beta chain (Hb-B) and transthyretin (TTR). After immunoaffinity extraction, SAP was detected with concomitant depletion of other proteins of higher concentration (FIG. 6B). Similarly, FIG. 6C shows an apparent peak for CRP, even though the level of this protein is 40-fold significantly lower than that of SAP in healthy individuals. Although the analysis showed minor peaks due to nonspecific binding of other plasma protein, they did not interfere with the unambiguous identification of CRP and SAP.

Comparison Between Nanoscale Particles and Microscale Particles

Recently, absorption of peptides/proteins onto microscale, reverse-phase magnetic particles was used to preconcentrate a dilute, contaminated sample for peptide mass mapping via MALDI analysis (see, Doucette et al., Anal. Chem., 2000, 72:3355-3362; Yaneva et al., Anal. Chem. 2003, 75:6437-6448; and Villanueva et al., Anal. Chem., 2004, 76:1560-1570; all of which are herein incorporated by reference). Approaches that conjugate antibody to microbeads have been reported to capture antigens of interest, yet these direct covalent conjugation procedures suffer from high background from non-specific binding and low signal-to-noise ratio (see, Peter, et al., Anal. Chem., 2001, 73:4012-4019, herein incorporated by reference). Thus, we compared microscales particle and nanoscale particles with regard to extraction efficiency and detection specificity. Anti-SAP antibody was conjugated to commercially available animated magnetic microbeads (2.8 µm) by the same modification process used for aminosilane mNPs. The amounts of immobilized anti-SAP antibodies were determined to be 47 µg/mg and 26 µg/mg for mNPs and microbeads, respectively, using the BCA protein assay. Thus, to ensure that equal amounts of antibody were used for antigen capture, we used a 1:1.8 volume ratio of nanoparticle/microbeads in parallel immunoassays.

As shown in FIGS. 6D and 6E, the signal intensity and signal-to-noise ratio were dramatically reduced in the mass spectrum of microbead-captured SAP and CRP compared with the nanoparticle experiments (FIGS. 6B and 6C). These results indicate that mNPs afford better affinity extraction of the targeted protein, thereby improving the detection limit (see, Soukka et al., Clin. Chem., 2001, 47:1269-1278, herein incorporated by reference). The fact that the same number of antibodies were immobilized on the surfaces of the nanoscale and microscale particles suggests that the multivalent interaction between the targeted antigen and antibody-conjugated nanoparticles yields superior sensitivity. Additionally, compared with the slightly reduced resolution using microbeads (see Papac et al., Anal. Chem. 1994, 66:2609-2613, herein incorporated by reference), both mass resolution and profile were maintained using mNPs, without apparent peak broadening and/or mass shift.

Concentration Effect for Plasma Protein Profiling

Figure 7:
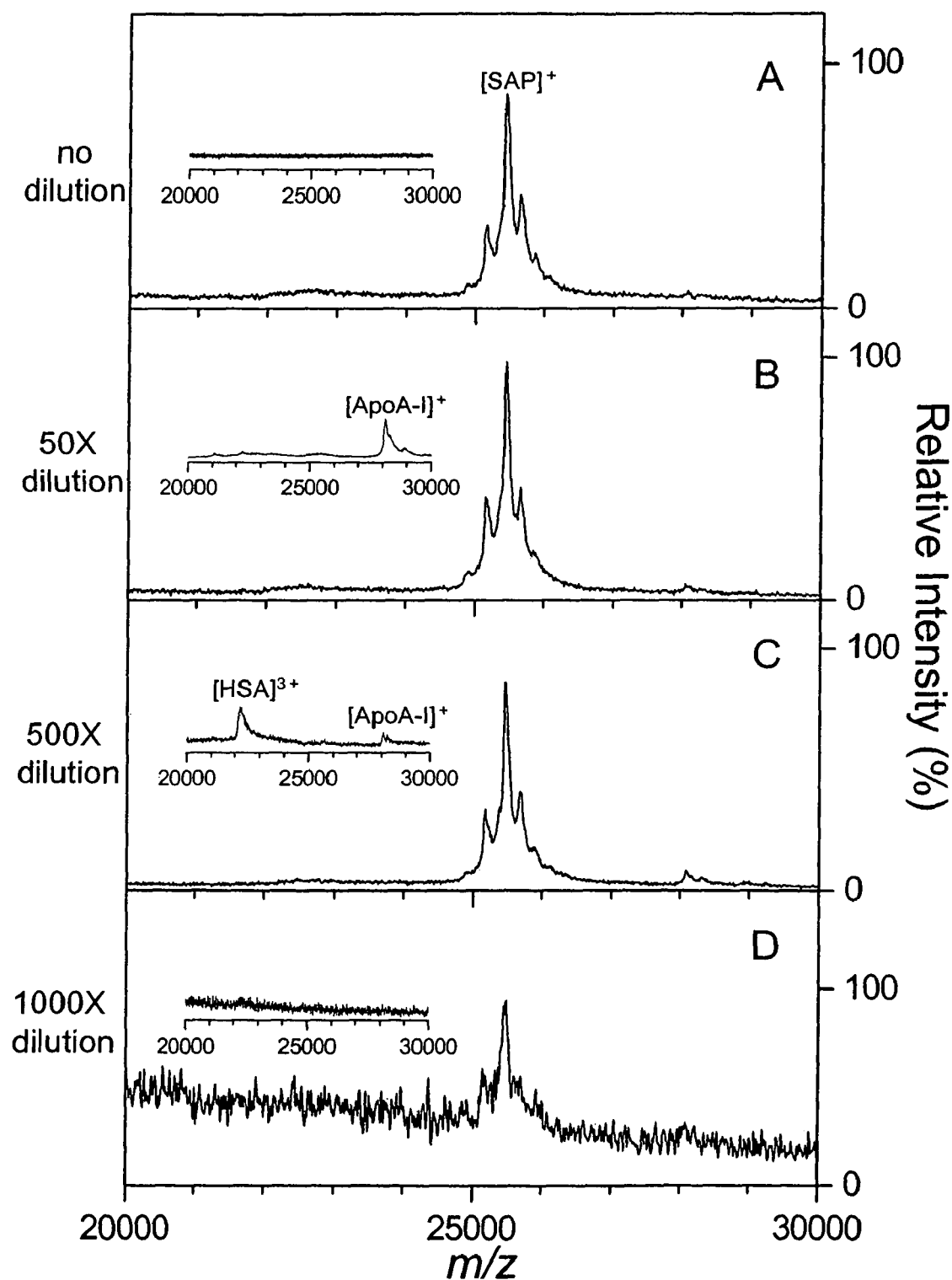
FIG. 7 shows a MALDI mass spectra of SAP extracted from 1 µL human plasma, either undiluted (A), diluted 50-fold (B), diluted 500-fold (C), or diluted 1000-fold (D), using anti-SAP-conjugated mNPs extraction. The inset of each panel shows the mass spectrum of solution prior to extraction.

Affinity extraction of targeted antigens using antibody-conjugated mNPs not only isolates but also preconcentrates low-level antigens onto the nanoprobe. To quantify this concentration effect, equal amounts of plasma (1 µL from each subject) were diluted 50-, 500- and 1000-fold in PBS and analyzed using the immunoassays of the present invention. The plasma SAP level of this subject had been rigorously determined to be 45.4±3.2 mg/L (1.8 µM). FIG. 7 shows the MALDI mass spectra of SAP extracted from each diluted sample. Incubation of the diluted plasma samples with the antibody-conjugated mNPs resulted in selective concentration of SAP, as demonstrated by the similar mass spectra profiles up to 500-fold dilution (FIGS. 7A, 7B and 7C). In the 1000-fold diluted sample (1.8 nM SAP), however, the captured antigen showed significantly lower intensity in the mass spectrum (FIG. 7D). It may be that this decreased recovery was a consequence of incomplete recovery of the mNPs from the curved wall of the microcentrifuge tube during the washing steps due to the large initial volume. These results demonstrate that 1 µL of plasma is sufficient to unambiguously identify an antigen of interest using immunoassays of the present invention. Despite the decreased recovery at 1000-fold dilution, the detection sensitivity (estimated to be 1.8 nM) was comparable to the sensitivity using a protein standard (SAP), demonstrating that the assay is refractory to the presence of highly abundant non-antigenic proteins, salts and buffers in plasma.

Analysis of Clinical Samples

Figure 8:
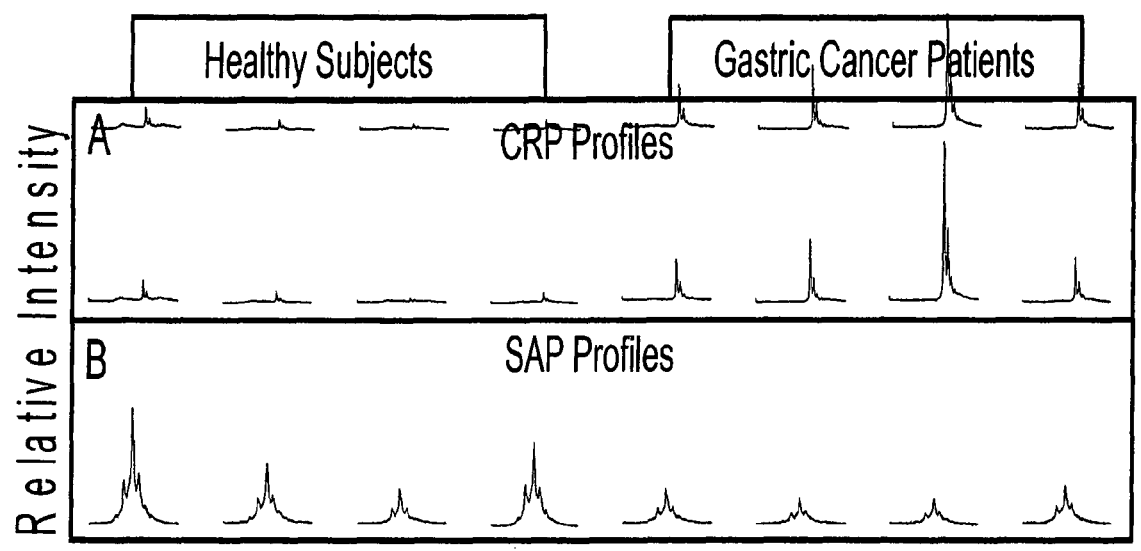
FIG. 8 shows results of screening of human plasma from healthy individuals and patients with gastric cancer using the nanoparticle-based mass spectrometric immunoassay. The MALDI mass spectra of CRP, in the m/z range of 20,000-25,000, are shown in panel (A). The MALDI mass spectra of SAP, in the m/z range of 24,000-27,000, are shown in panel (B).

The performance of mNP immunoassays was assessed using authentic clinical samples—plasma from 4 healthy individuals and 4 patients with gastric cancer (FIG. 8). CRP and SAP were detected in all the healthy individuals, despite the fact that the levels of a few of them were below the detection limit of ELISA (<0.159 mg/L) (see, Juan et al., Proteomics, 2004, 4:2766-2775, herein incorporated by reference). The measured intensities for CRP were considerably higher in the gastric cancer patient samples than in the healthy control samples. By contrast, the SAP levels in the patients were lower than those in the healthy individuals. These observed differences in protein levels are consistent with the differential protein profiles of gastric cancer patients as assessed by comparative proteomic approaches (see, e.g., Solakidi et al., Clin. Biochem. 2004, 37:56-60, herein incorporated by reference). It is noted that the ion intensity measured by the nanoparticle-based assay using a 20 µL sample correlated with the concentration measured by ELISA, indicating that mNP immunoassay would be useful for quantitative protein profiling.

Example 2

Mass Spectrometric Detection with Antibody Conjugated Magnetic Nanoparticles Blocked with Methoxy-Ethylene Glycol This example describes construction of various antibody conjugated magnetic nanoparticles blocked with methoxy-ethylene glycol and their use to detect antigens in biological samples using mass spectrometry. In particular, this example describes the construction of magnetic nanoparticles conjugated to anti-SAP or anti-CRP antibodies and the use of these nanoparticles to detect SAP and CRP in human plasma samples using mass spectrometry.

Construction of MEG Protected Antibody Encapsulated Magnetic Nanoparticles

The synthesis of antibody-conjugated ion oxide NP is illustrated in FIG. 9. Aminated $Fe_3O_4$ nanoparticles (1 mg) was dispersed into 250 uL dimethyl sulfoxide (DMSO) and sonicated for 30 minutes. After sonicating, suberic acid bis N-hydroxysuccinimide ester (DSS) (10 mg, 0.03 mmol) was added to the solution and stirred for one hour at room temperature. The resulting nanoparticles were washed with DMSO (100 uL) for 3 times to remove excess DSS. 50 uL of anti-SAP (6.7 mg/1 mL) antibody was added to the black solid and then shaked at 4° C. for 30 minutes. Then, 50 uL of 80 mM compound 1 (MEG; methoxy ethylene glycol) was added to the mixture and followed by shaking for 12 hours at 4° C. After filtration, the nanoparticle was washed with PBS (100 uL, PH 7.4, 0.1 M) for 5 times to give anti-SAP MNP as black powder. Anti-CRP encapsulated mNPs blocked with MEG were constructed in similar fashion.

Immunoaffinity Identification by MALDI-TOF

Immunoagglutination. Aliquots (2 mL, 5 mg/mL) of functionalized MNPs were added in 60 mL phosphate buffered saline (PBS, pH~7.4) solution composed of human plasma (5 mL). The solution was incubated at room temperature for 1 hour with slow rotation. After that, the mNPs were agglutinated at the wall of eppendorf using a magnetic separator so that the supernatant was removed by pipette. During the washing steps, the MNPs were resuspended sequentially in 100 mL of Tris buffer (100 mM), TBS buffer (with 0.05% Tween 20), and 25 mM $NaHCO_3$(aq) and agglutinated to remove supernatant. In the final step, the MNPs were thoroughly and directly transferred to a MALDI plate. Aliquots (1 mL) of matrix solution (sinapinic acid, 10 mg/mL containing 50% acetonitrile, 50% water, and 0.1% trifluoroacetic acid) were applied and subsequently analyzed by MALDI MS. Mass Spectrometry. MALDI-TOF mass spectra were acquired by a mass spectrometer (Voyager-DE STR, PerSeptive Biosystems, USA) equipped with a 337 nm nitrogen laser source. Measurements were taken in linear, positive ion mode at 25 kV acceleration voltage, 90% grid voltage, 0.3% guide wire voltage, 650 ns delayed ion extraction and a low mass gate of 5000 Da. The cytochrome c (M.W.=12361 Da), myoglobin (M.W.=16952 Da) were used as external standards for mass calibration. A typical mass spectrum was obtained by average of 250 laser shots followed by noise reduction and Gaussian smoothing using Data Explorer software (Applied Biosystems, Foster City, Calif., USA).

Results and Discussion

Figure 10:
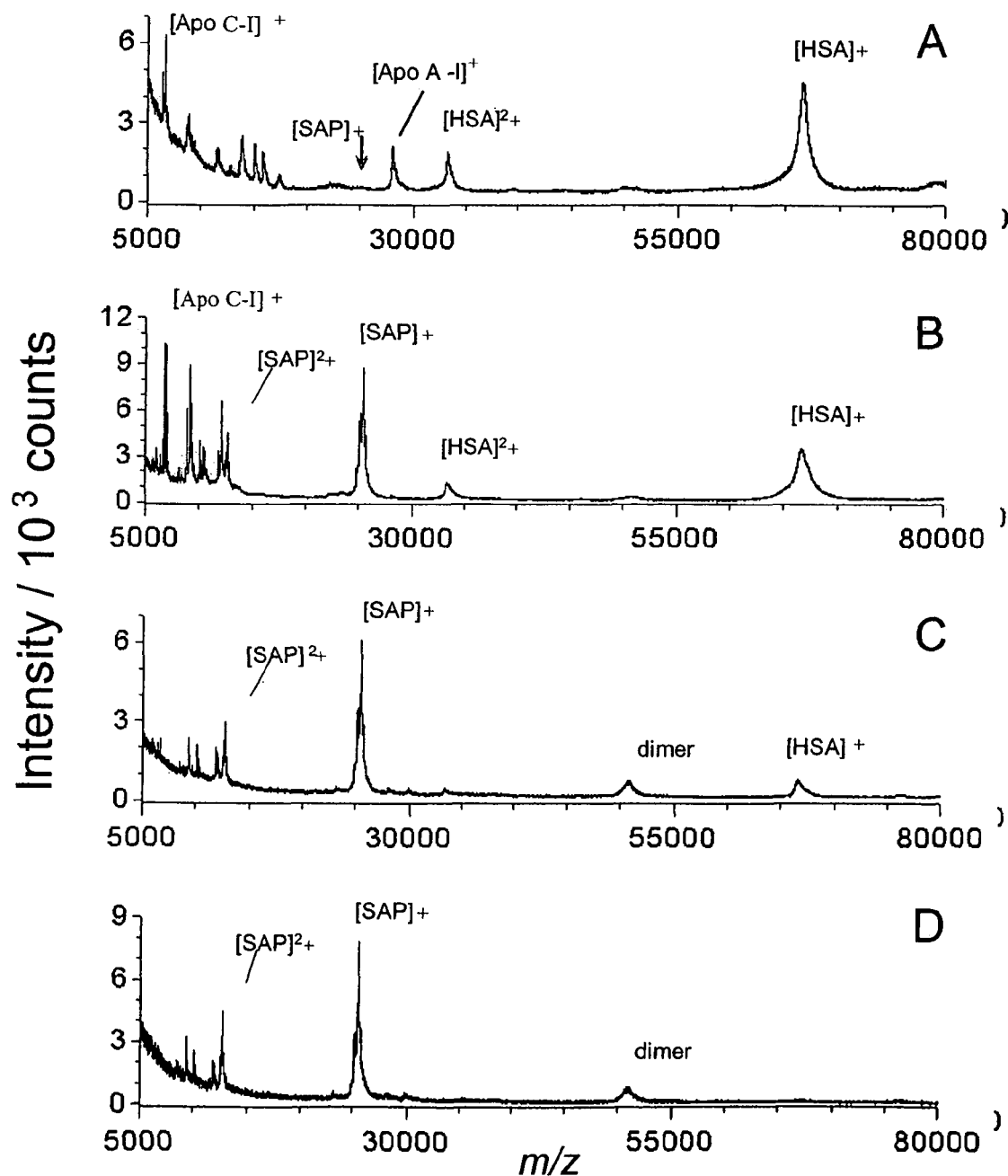
FIG. 10 shows a MALDI-TOF mass spectra of human plasma from immunoaffinity extraction with anti-SAP MNP: (A) 25-fold dilution of human plasma (B) extraction by anti- SAP-MNP (w/o blocking); (C) extraction by anti-SAP MNP (BSA blocking); and (D) extraction by anti-SAP MNP (MEG blocking).

Anti-SAP mNP was tested for its ability to bind SAP in plasma of healthy humans. SAP is a biomarker related to Alzheimer's disease and type 2 diabetes, with a concentration of 0-40 mg/L in blood of healthy humans. Anti-SAP mNP was incubated with 5 mL plasma for the SAP concentration as 40 mg/L. After immunoaffinity interaction, the SAP-nanoparticle complexes were separated by the magnet and the non-antigenic contaminants were subsequently washed out with 100 mM Tris buffer, TBS buffer (Tris buffered saline: 50 mM Tris-HCl, 0.85% NaCl, pH 7.5) and 25 mM $NaHCO_3$ (aq). Finally, the captured targeted antigen on nanoparticles was directly analyzed by MALDI-TOF MS. The MALDI mass spectrum of human plasma prior to immunoaffinity extraction is shown in FIG. 10A, and revealed that the most abundant proteins were human serum albumin (HAS, 66 KDa) and Apo protein C-I (Apo C-I, 6.6 KDa). The targeted SAP was barely detectable on mass analysis. However, after immunoaffinity extraction by anti-SAP MNP, the SAP peak alone was found in the mass spectrum, as shown in FIG. 10B. Thus, this method successfully demonstrated enrichment of the targeted protein and depletion of contaminants, including other abundant non-antigenic proteins, salts, and buffer.

Various extents of nonspecific binding with HSA and Apo C-I were observed in mass spectra, as shown in FIG. 10B, when anti-SAP MNP was used. In bioassays, bovine serum albumin (BSA) is usually used as a blocking agent to prevent non-specific interactions. Thus, anti-SAP MNP was further coated with BSA and then tested for specificity in immunoaffinity extraction. However, good suppression of the HSA peak was not obtained (FIG. 1C). Therefore, the small methoxy-ethylene glycol with terminal amino functionality (MEG, compound 1 in FIG. 9) was synthesized and reacted with the terminal N-hydroxysuccinimide linkers on nanoparticles which had been incubated with anti-SAP antibody for 30 minutes at 4° C. The new blocking reagent (MEG) exhibited markedly improved specificity and prominent depletion of non-specific binding (FIG. 10D). Only 6 mg of the MNPs was used to obtain the signal of target antigen with an infinitesimal amount of targeted protein (66 pg/mL) without detectable nonspecific binding.

Figure 11:
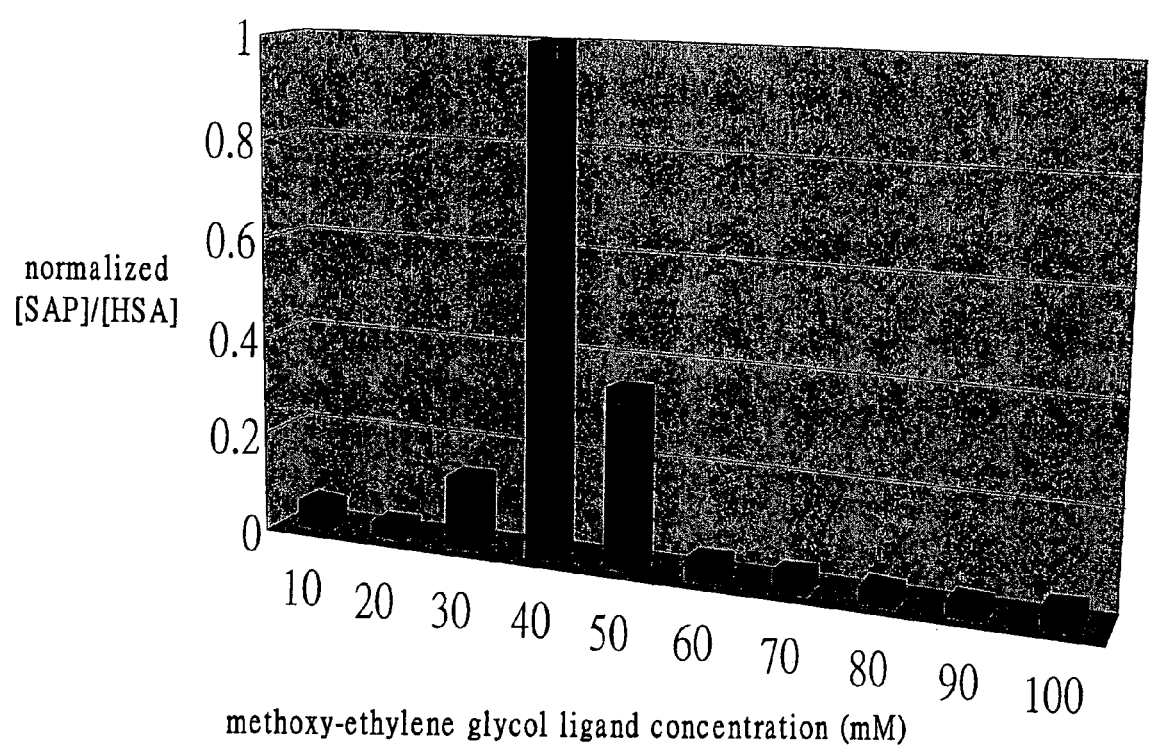
FIG. 11 shows the concentration effect of MEG blocking of mNPs.

To optimize MEG conjugation on the MNP surface for depletion of non-specific interaction, a series of concentrations (from 10 mM to 100 mM) of MEG were reacted with anti-SAP MNP. Results showed that depletion of non-specific binding of MEG-coated anti-SAP MNP with HSA was MEG-concentration-dependent. MEG at 40 mM exhibited the highest ratio of specific to non-specific binding, as shown in FIG. 11. Although different concentrations of MEG were used to react with activated ester on the mNP surface, the amounts of anti-SAP antibody on MNP were the same in each experiment. These results suggested that the maximum amount of antibody that was assembled on mNP within about 30 minutes.

Figure 12:
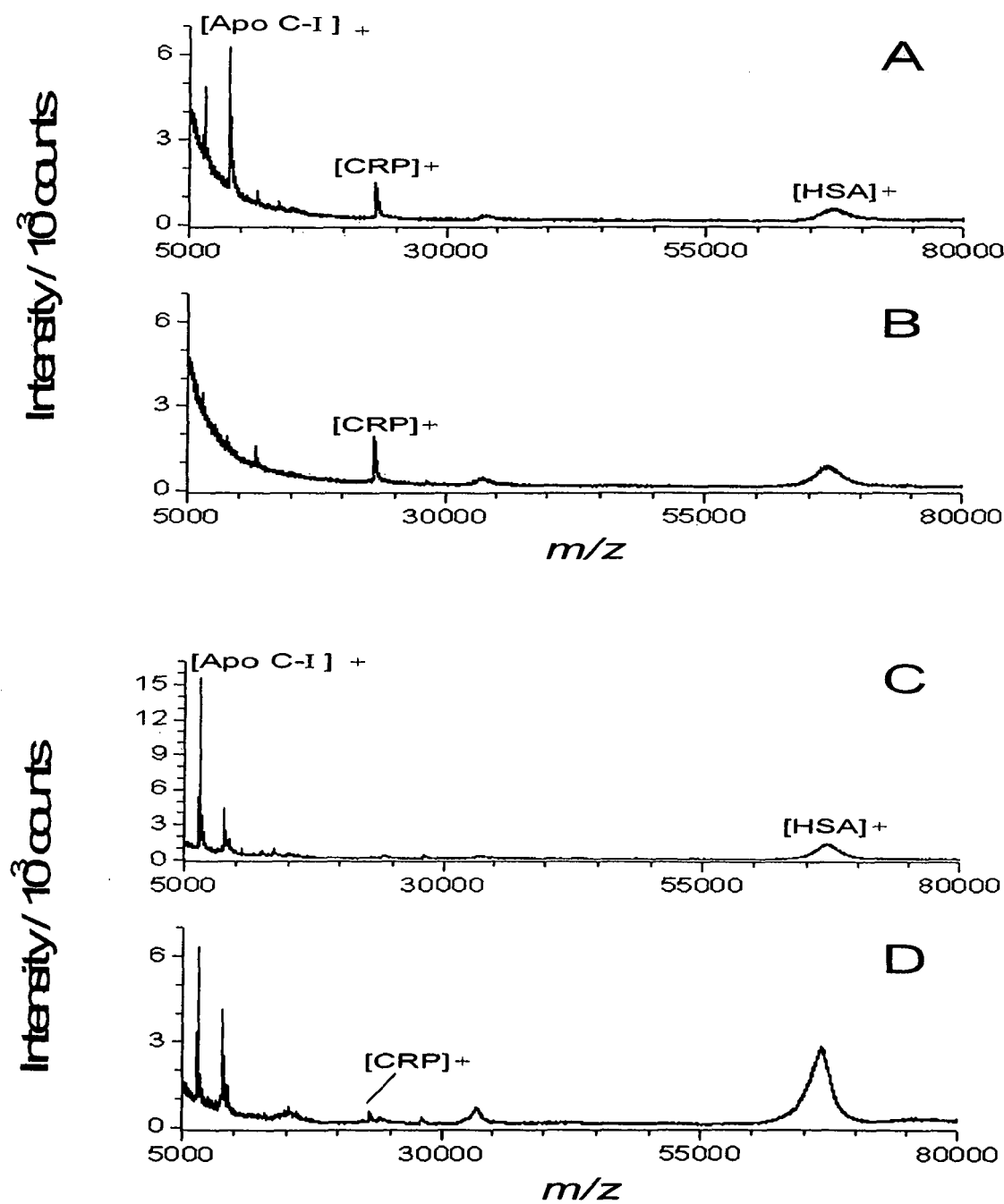
FIG. 12 shows a MALDI-TOF MS spectrometry of (A) human serum (containing CRP 5 mg/L) extracted by anti-CRP-MNP (w/o blocking) (B) human serum (containing CRP 5 mg/L) extracted by anti-CRP-MNP (with 30 mM MEG blocking) (C) the extreme low abundant CRP (<0.9 mg/L) of healthy human serum extracted by anti-CRP-MNP (w/o blocking) (D) the extreme low abundant CRP (<0.9 mg/L) of healthy human serum extracted by anti-SAP-MNP (with 30 mM MEG blocking).

Next, C-reactive protein (CRP) was tested in order to demonstrate the general applicability of this method. CRP is an exquisitely sensitive systemic marker of acute-phase inflammatory response, tissue injury, and coronary artery disease (see, e.g., Berton et al., Am. Heart. J., 2003, 145:1094-1101, herein incorporated by reference). In recent studies, it has been shown that CRP concentration rises from less than 0.05 mg/L to more than 500 mg/L in serum (Pepys et al., J. Clin. Invest., 2003, 111, 1805-1812, herein incorporated by reference) with an acute-phase stimulus, and the level of CRP has also been found to correlate with the severity, extent, and progression of many different diseases. With the need for quick response and assay specificity, we first prepared anti-CRP-mNP for detecting CRP present in low abundance in a cancer patient's serum (5 mL plasma sample was used), which featured a CRP concentration of 40 mg/L by ELISA. Following extraction with anti-CRP MNP, though CRP was detected as the most prominent peak by this non-MEG protected MNP, nonspecific binding with Apo C-I was still observed (FIG. 12A). Following conjugation with 30 mM of MEG, however, the MEG-protected anti-CRP-MNP successfully decreased the nonspecific binding peak and enhanced the CRP peak (FIG. 12B). Surprisingly, MEG-protected anti-CRP-MNP could detect low CRP concentration present in minute amounts (<0.9 mg/L) in healthy individuals (5 uL plasma sample was used), though this is difficult to achieve with the ELISA assay used in clinical setting. This is shown in FIG. 12C (without MEG blocking) and FIG. 12D (with MEG blocking).

Example 3

Figure 13:
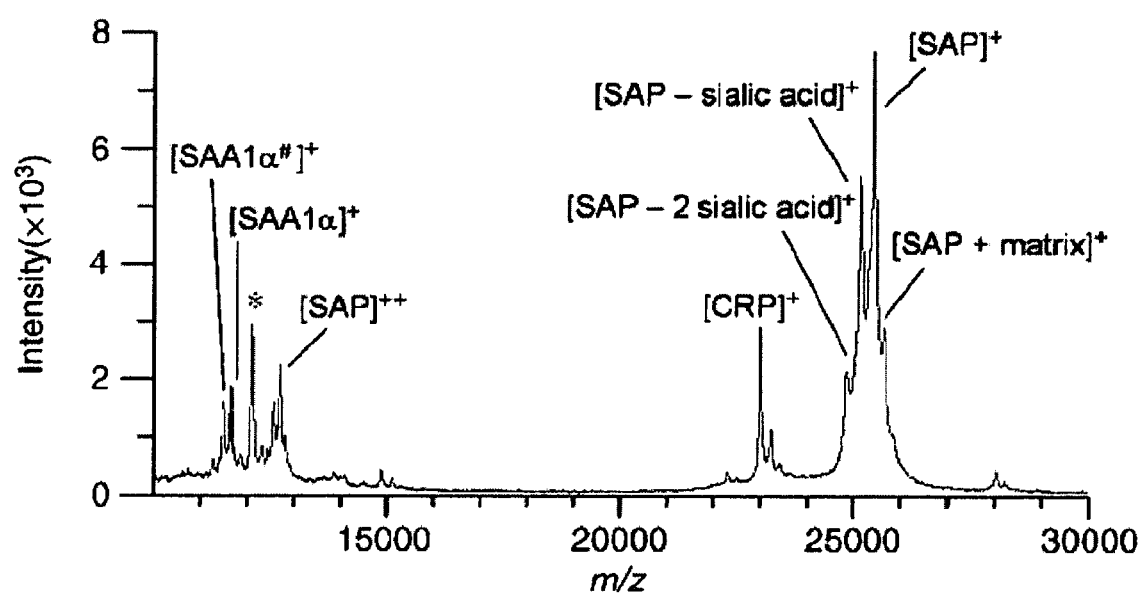
FIG. 13 shows a MALDI-TOF mass spectrum obtained from multiplexed immunoassay of SAA, CRP, and SAP from human plasma sample as described in Example 3.

Multiplexed Mass Spectrometric Detection with Antibody Conjugated Magnetic Nanoparticles This Example describes the multiplex detection of three different target analytes simultaneously using mass spectrometry and MEG-protected antibody conjugated nanoparticles. After affinity extraction with a mixture of anti-SAA, anti-CRP, and anti-SAP MNPs, SAA, CRP, and SAP were selectively and simultaneously detected in 1 mL plasma (100-fold dilution) obtained from a healthy individual, as shown in FIG. 13. The asterisk represents the impurity peak generated from commercially available anti-SAP antibody. The heterogeneous profile of native SAP and deglycosylated SAP variants (from removal of the terminal sialic acid residue) was clearly resolved. Meanwhile, the truncated forms of SAA isotypes were present in the plasma from a healthy individual. The results of this example demonstrate the ability of the magnetic nanoparticles of the present invention to be detected by mass spectrometry in a multiplex manner.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method of assaying a target analyte in a sample comprising the steps of:
   a) providing a composition comprising antibody-conjugated magnetic nanoparticles (Ab-mNPs), wherein each of the Ab-mNPs comprises:
      i) a core iron oxide nanoparticle ranging in size from 0.1 to 500 nm;
      ii) cross-linkers, covalently conjugated to the surface of the core nanoparticle;
      iii) antibody molecules specific for a target analyte, covalently conjugated to the cross-linkers; and
      iv) methoxy ethylene glycol having the structure $H_3C-O-CH_2CH_2-O-CH_2CH_2-O-CH_2CH_2-NH_2$ covalently conjugated through the amine group to cross-linkers that are unconjugated to the antibody molecules;
   b) exposing a sample that may contain the target analyte to the Ab-mNPs to allow the target analyte to be captured by the Ab-mNPs;
   c) subjecting the Ab-mNPs and the sample from step (b) to a magnetic field to separate the Ab-mNPs and the captured target analyte from the rest of the sample; and
   d) performing mass spectrometry on the Ab-mNPs and the captured target analyte from step (c) to obtain a mass spectrum for assaying the target analyte;
   wherein the target analyte is a compound selected from the group consisting of a protein, a polypeptide and a peptide.

2. The method of claim 1, wherein the sample is obtained from a patient suspected of having, a change in the plasma level of the target analyte.

3. The method of claim 2, wherein the target analyte is a compound selected from the group consisting of serum amyloid P component (SAP) and C-reactive protein (CRP).

4. The method of claim 2, further comprising the step of comparing the mass spectrum of the target analyte of the sample obtained from the patient with that obtained from a healthy subject to detect whether there is a change in the profile of the target analyte in the patient.

5. The method of 1, wherein the providing step further comprises the step of synthesizing the Ab-mNPs, which comprises:
   reacting the methoxy ethylene glycol with magnetic nanoparticles to obtain the Ab-mNPs with the methoxy ethylene glycol covalently conjugated through the amine group to the cross-linkers that are unconjugated to the antibody molecules wherein each of the magnetic nanoparticles in the reacting step comprises:
      i) a core iron oxide nanoparticle;
      ii) cross-linkers, conjugated to the surface of the core nanoparticles; and
      iii) antibody molecules specific for the target analyte, covalently conjugated to the cross-linkers.

6. The method of claim 5, wherein the concentration of the methoxy ethylene glycol for reacting with the magnetic nanoparticles is between 30 and 50 mM.

7. The method of claim 1, wherein the sample is from a cancer patient.

8. The method of claim 1, wherein the target analyte is a protein selected from the group consisting of serum amyloid P component (SAP), C-reactive protein (CRP), serum amyloid A protein (SAA), myoglobin, enolas (Eno), and apolipoprotein.

9. The method of claim 1, wherein the target analyte is a human plasma protein.

10. The method of claim 2, wherein the sample is obtained from a cancer patient.

11. A method for assaying multiplex target analytes in a sample comprising the steps of:
   a) providing a composition comprising more than one kind of Ab-mNPs, of which each kind has a different antibody conjugated to it, and each of the Ab-mNPs comprises:
      i) a core iron oxide nanoparticle ranging in size from 0.1 to 500 nm;
      ii) cross-linkers, conjugated to the surface of the core nanoparticle;
      iii) antibody molecules specific for one of the multiplex target analytes, covalently bound to the cross-linkers; and
      iv) methoxy ethylene glycol having the structure $H_3C-O-CH_2CH_2-O-CH_2CH_2-O-CH_2CH_2-NH_2$ covalently conjugated through amine group to the cross-linkers that are unconjugated to the antibody molecules;
   b) exposing a sample that may contain the multiplex analytes to the Ab-mNPs to allow the multiplex analytes to be captured by the Ab-mNPs;
   c) subjecting the Ab-mNPs and the sample from step (b) to a magnetic field to separate the Ab-mNPs and the captured multiplex analytes from the rest of the sample; and
   d) performing mass spectrometry on the Ab-mNPs and the captured multiplex target analytes from step (c) to obtain mass spectra for assaying the multiplex target analytes;
   wherein the target analytes are compounds selected from the group consisting of proteins, polypeptides and a peptides.

12. The method of claim 11, wherein the sample is from a patient suspected of having a change in the plasma level of the target analytes.

13. The method of claim 12, wherein the target analytes are human plasma proteins.

14. The method of claim 13, further comprising the step of comparing the mass spectra of the target analytes of the sample obtained from the patient with those obtained from a healthy subject to detect whether there is a change in the profile of the target analytes in the patient.

15. The method of claim 11, wherein the sample is obtained from a cancer patient.

* * * * *